US011937956B2

(12) United States Patent
Beekman

(10) Patent No.: US 11,937,956 B2
(45) Date of Patent: Mar. 26, 2024

(54) SPECT-SCANNER AND COLLIMATOR

(71) Applicant: MILABS B.V., Utrecht (NL)

(72) Inventor: Frederik Johannes Beekman, Utrecht (NL)

(73) Assignee: MILABS B.V., Utrecht (NL)

(*) Notice: Subject to any disclaimer, the term of this patent is extended or adjusted under 35 U.S.C. 154(b) by 399 days.

(21) Appl. No.: 17/433,483

(22) PCT Filed: Feb. 24, 2020

(86) PCT No.: PCT/NL2020/050117
§ 371 (c)(1),
(2) Date: Aug. 24, 2021

(87) PCT Pub. No.: WO2020/175985
PCT Pub. Date: Sep. 3, 2020

(65) Prior Publication Data
US 2022/0133246 A1    May 5, 2022

(30) Foreign Application Priority Data

Feb. 25, 2019 (NL) ......................... 2022634
Jan. 29, 2020 (NL) ......................... 2024784

(51) Int. Cl.
*G21K 1/02* (2006.01)
*A61B 6/03* (2006.01)

(52) U.S. Cl.
CPC ............ *A61B 6/037* (2013.01); *A61B 6/4057* (2013.01)

(58) Field of Classification Search
CPC .. A61B 1/00; A61B 6/037; A61B 6/06; A61B 6/4291; G21K 1/046; G21K 1/04;
(Continued)

(56) References Cited

U.S. PATENT DOCUMENTS

| 5,583,343 A | 12/1996 | Dilmanian et al. |
| 2009/0022278 A1* | 1/2009 | Hugg ........................ A61B 6/06 378/149 |
| 2016/0077217 A1 | 3/2016 | Shahar |

FOREIGN PATENT DOCUMENTS

| EP | 2 073 039 A1 | 6/2009 |
| EP | 2 360 494 A2 | 8/2011 |

(Continued)

OTHER PUBLICATIONS

International Search Report for PCT/NL2020/050117 dated Mar. 24, 2020.

(Continued)

*Primary Examiner* — Don K Wong
(74) *Attorney, Agent, or Firm* — Birch, Stewart, Kolasch & Birch, LLP

(57) ABSTRACT

A SPECT scanner for making images of an object using gamma radiation comprises a collimator that extends along a longitudinal direction around an object space and that comprises a set of pinholes for the gamma radiation, a detection device for gamma radiation that is allowed to pass through from the object space by the pinholes, and an object carrier for bringing the object into the object space along the longitudinal direction. At least one pinhole is provided in a pinhole body that is rotatable in the collimator around an axis of rotation. Because the pinholes themselves rather than the collimator are made rotatable, the entire object space with the object therein can be advantageously scanned without having to move the object. The properties of the collimator can also easily be adjusted, even during scanning.

20 Claims, 11 Drawing Sheets

(58) Field of Classification Search
CPC .......... G21K 1/025; G21K 1/02; G01T 3/001; G01T 3/085; G01T 3/065
See application file for complete search history.

(56) References Cited

FOREIGN PATENT DOCUMENTS

EP         2 482 101 A1   8/2012
WO    WO 2007/105942 A2   9/2007

OTHER PUBLICATIONS

Moore et al., "Design of a dual-resolution collimator for preclinical cardiac SPECT with a stationary triple-detector system", Medical Physics, AIP, Melville, NY, Nov. 3, 2016, vol. 43, No. 12, pp. 6336-6346.
Rittenbach et al., "The Design of Optimal Multipinhole Collimators for a Seamless SPECT Detector Ring", 2011 IEEE Nuclear Science Symposium Conference Record, Oct. 23, 2011, pp. 3402-3405.
Search Report for NL application No. 2022634 dated Feb. 25, 2019.
Written Opinion of the International Searching Authority for PCT/NL2020/050117 (PCT/ISA/237) dated Mar. 24, 2020.

* cited by examiner

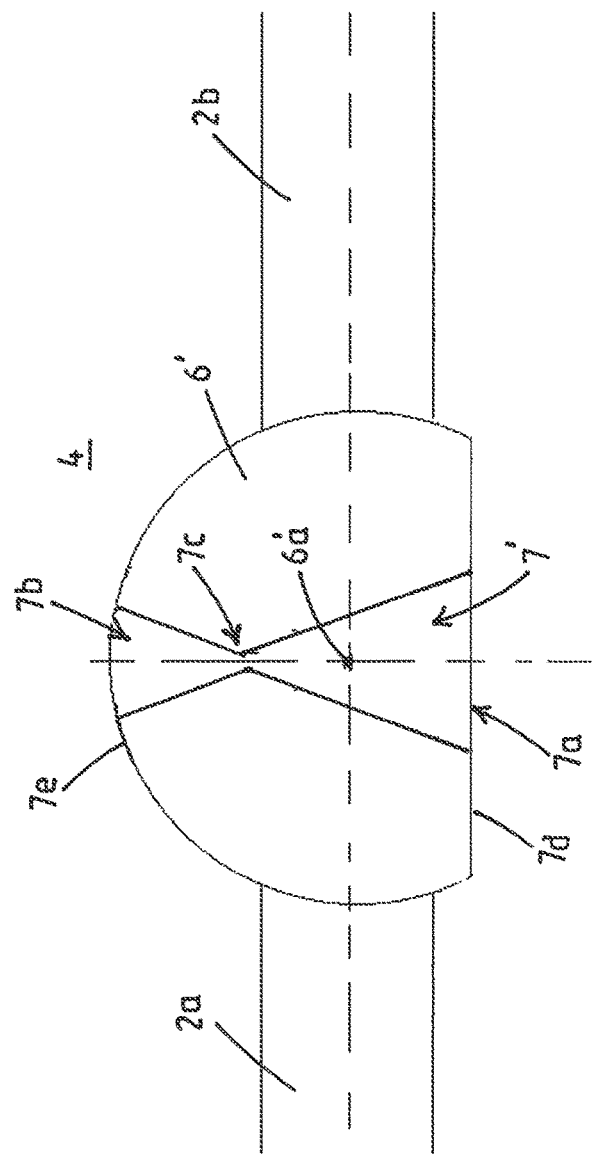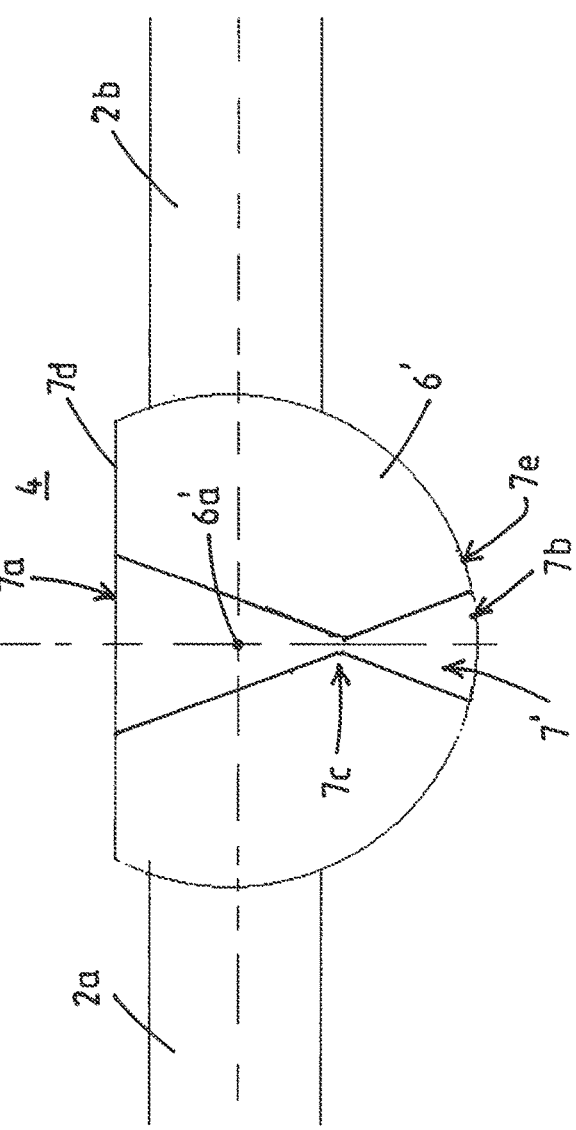

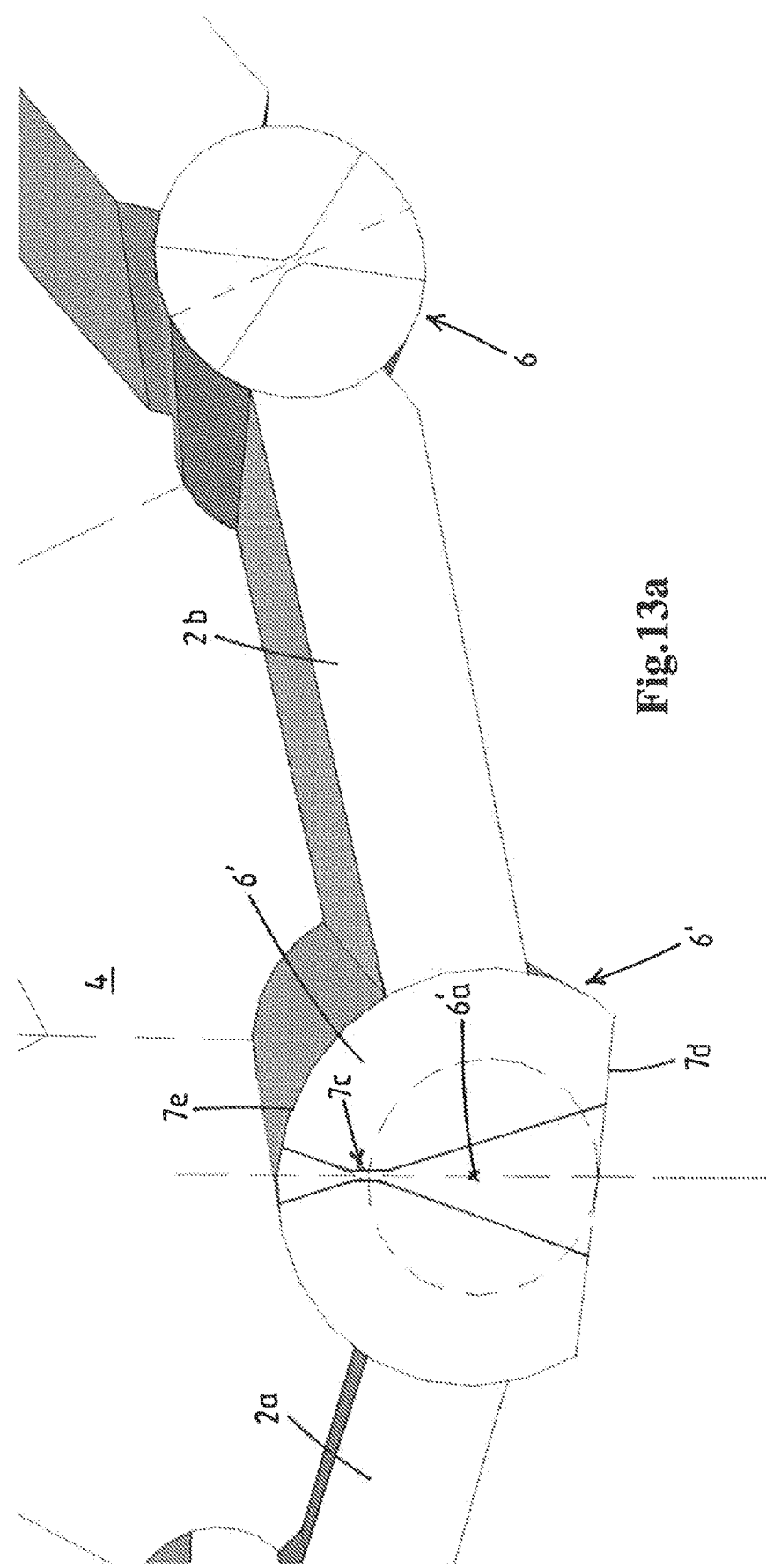

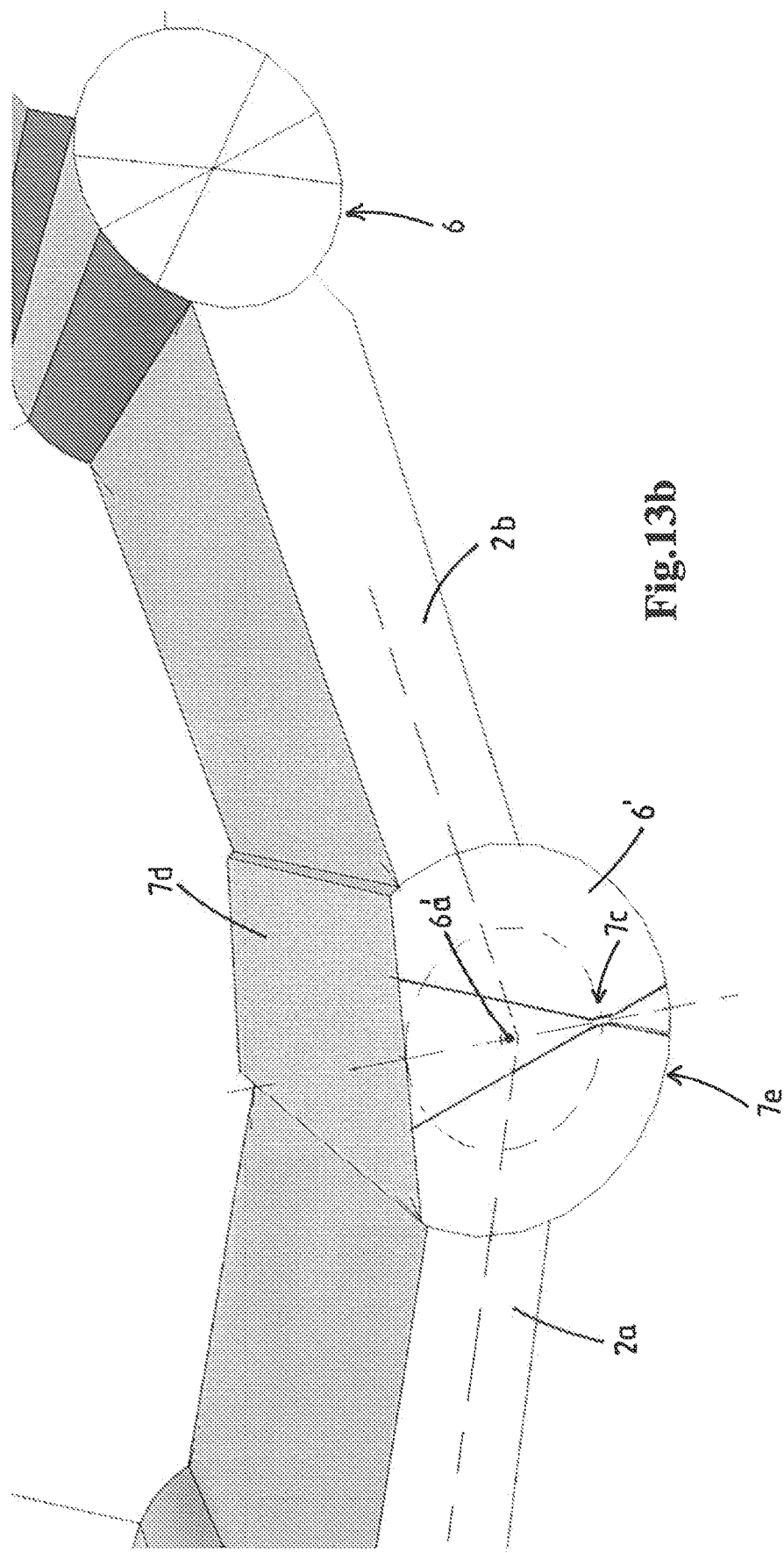

SPECT-SCANNER AND COLLIMATOR

FIELD OF THE INVENTION

The present invention relates to a SPECT scanner and a SPECT scanner collimator for making images of an object using gamma radiation.

BACKGROUND OF THE INVENTION

SPECT scanners (single-photon emission computed tomography scanners) are instruments that are currently in widespread use for collecting 3D image data on specific tissue structures and the like using gamma emitters introduced into an object. For this purpose, multiple 2D images (projections) are taken from different angles. The 2D images are then processed into 3D image data using a computer.

EP 2482101 discloses a SPECT scanner with clusters of pinholes, wherein switching from the open to the closed condition, i.e. the transmission condition, of at least one pinhole of a cluster is selectively adjustable by means of an accompanying pinhole shutter device.

EP 2360494 discloses a SPECT scanner wherein the collimator is configured such that the focus volume thereof lies eccentrically with respect to a centre line that extends in a longitudinal direction through a centre of gravity of a cross-section of the object space. Here, the focus volume is defined as the volume of the space that can be seen by all of the pinholes of the collimator as a whole, i.e. the overlap of all of the fields of view of the pinholes.

For example, the object to be examined is a small animal, such as a mouse or a rat, for example in the context of a preclinical research. In another example, the object is a human. For example, the object space is adapted for receiving a human head, or in a larger embodiment, the torso of the person. In the latter case, it is often provided that the person is moved feet first into the object space until the torso is reached, so that the object space and the collimator do not have to be large enough to accommodate the shoulders.

A drawback of known SPECT scanners is that they do not always have an optimum combination of sensitivity, selectivity/flexibility, and size for the area to be scanned.

OBJECT OF THE INVENTION

It is an object of the present invention to provide an improved SPECT scanner and a SPECT scanner collimator. For example, it is an object to provide a SPECT scanner and a corresponding collimator that make it easily possible to displace the focus volume within the space. For example, it is an object to provide a more universally applicable solution. For example, it is an object to provide a SPECT scanner and a corresponding collimator that make it easily possible to acquire successive images wherein one or more properties of the collimator are different, for example regarding sensitivity and/or selectivity/flexibility and/or size for the area to be scanned.

SUMMARY OF THE INVENTION

The invention provides, according to a first aspect thereof, a SPECT scanner for making images of an object using gamma radiation emitted by the object, comprising:
 an object space with a longitudinal direction,
 an object carrier configured for bringing an object into the object space in said longitudinal direction and for positioning the object in the object space,
 a collimator that extends in a circumferential direction thereof at least partially around the object space, wherein the collimator comprises a set of multiple pinholes each of which comprises a field of view with a main pass-through direction for gamma radiation emitted by the object,
 a detection device with at least one detector configured for detecting gamma radiation that is allowed to pass through from the object space by one or more of the pinholes, wherein the collimator is provided between the object space and the at least one detector,
 wherein the collimator is provided with at least one rotatable pinhole body with at least one pinhole therein, which pinhole body is rotatably arranged in the collimator around at least one corresponding axis of rotation.

By rotation of a pinhole body, the one or more pinholes provided therein are rotated with respect to the rest of the collimator. For example, multiple pinholes are provided in one pinhole body, for example one or more rows of pinholes wherein each row extends essentially in the longitudinal direction.

In an embodiment, the collimator comprises multiple rotatable pinhole bodies that are arranged around the object space distributed in the circumferential direction, each of which rotatable pinhole bodies has at least one pinhole therein, wherein each rotatable pinhole body is rotatably arranged in the collimator around at least one corresponding axis of rotation, and wherein the axes of rotation of the pinhole bodies are apart from one another, preferably wherein each rotatable pinhole body is rotatably arranged in the collimator exclusively about an axis of rotation that extends essentially parallel to said longitudinal direction.

In an embodiment, the collimator in the circumferential direction thereof forms a closed loop around the object space, wherein multiple rotatable pinhole bodies are provided in the collimator distributed in the circumferential direction of the loop, each of which rotatable pinhole bodies has at least one pinhole therein, wherein each rotatable pinhole body is rotatably arranged in the collimator around at least one corresponding axis of rotation, preferably wherein each rotatable pinhole body is rotatably arranged in the collimator exclusively about an axis of rotation that extends essentially parallel to said longitudinal direction. For example, at least six rotatable pinhole bodies are provided in a collimator that forms a closed loop around the object space.

In an embodiment, the collimator, seen in the circumferential direction, comprises a series of multiple collimator elements and at least one rotatable pinhole body, wherein said rotatable pinhole body is arranged between adjacent collimator elements, which rotatable pinhole body has at least one pinhole therein and is rotatably arranged in the collimator around a single corresponding axis of rotation that extends essentially parallel to said longitudinal direction. Preferably, it is herein provided that adjacent collimator elements of the series are pivotable with respect to one another about a pivot axis that extends essentially parallel to said longitudinal direction. For example, adjacent collimator elements are interconnected by a pivot mechanism that forms a pivot axis running parallel to said longitudinal direction. Preferably, the cross-section of the collimator, seen perpendicular to the longitudinal direction, is adjustable by pivoting the collimator elements relative to one another. In a practical embodiment, a pivot axis between adjacent collimator elements coincides with the axis of rotation of a pinhole body.

In an embodiment, each of the one or more, for example all, rotatable pinhole bodies is/are configured as an elongated solid rod of collimator material, for example tungsten, which rod is rotatable in the collimator about a longitudinal axis thereof. For example, such a rod has a diameter of at least 3 cm, for example between 3 and 10 cm.

In an embodiment, the collimator is provided with at least one rotatable pinhole body with at least one pinhole therein, wherein the at least one pinhole extends from a first opening on a first side of the pinhole body to a second opening on a second side of the pinhole body located opposite the first side, wherein the at least one pinhole has a smallest cross-sectional part that defines the smallest cross-section for gamma radiation of the pinhole and is located at a distance from the first opening and from the second opening of the pinhole, wherein the smallest cross-sectional part, seen in the direction between the first opening and the second opening of the pinhole, is located at a distance from the axis of rotation of the pinhole body, such that—during use—the distance between the smallest cross-sectional part of the pinhole and an object positioned by the object carrier is variable by selectively rotating the pinhole body with the first side thereof or the second side thereof toward the object space. This solution makes it, for example, possible to easily adjust the effective distance between the smallest cross-sectional part of the pinhole and the object, for example in order in this manner to set imaging properties of the collimator, such as for example the effective field of view. For example, the pinhole body is rotatable over at least 180° around the axis of rotation. For example, the variation of the distance between the smallest cross-sectional part of the pinhole and an object positioned by the object carrier produced by means of the above-mentioned rotation is at least 10 mm. It will be apparent that another size of variation is also possible by suitably configuring the pinhole body and the pinhole therein, for example by means of a large cross-section of the pinhole body.

For example, the pinhole body rotatable about an axis has a diameter in a plane perpendicular to the axis, optionally configured as circular segment shape, that is larger than the thickness of adjacent plate-shaped collimator elements, for example with respect to mutually pivotable plate-shaped collimator elements.

In an embodiment, the rotatable pinhole body is cylindrical with an essentially circular cross-section. Other embodiments are also conceivable, and even possibly advantageous, such as for example a circular segment-shaped cross-section.

For example, one or more rotatable pinhole bodies is/are configured such that the first side of the pinhole body is at a smaller distance from the axis of rotation of the body than the second side, wherein the pinhole has a first opening in the first side and the pinhole has a second opening in the second side. For example, the first side is an essentially flat side, wherein the rest of the perimeter of the pinhole body is possibly circular arc-shaped. In yet another version, both the first side and the second side of the pinhole body are essentially flat, for example parallel. Here, it is possible for the side surfaces of the pinhole body lying in between to be circular arc-shaped, preferably with an equal radius around the axis of rotation.

A rotatable pinhole body is placed for example in a corresponding elongated slot in the collimator. The slot can, for example, be present at the site where two neighbouring collimator elements are adjacent to each other, seen in a circumferential direction of the collimator, for example between adjacent pivoting collimator elements as will be further explained herein. An alternative collimator has a rigid collimator body that extends as a whole around at least one part of the perimeter of the object space, for example as a closed loop, and is non-adjustable with respect to the cross-section, e.g. is tubular or semi-cylindrical in cross-section, wherein multiple elongated slots are configured in said rigid collimator body at a distance from one another, preferably parallel to one another and aligned in the longitudinal direction, with said slots each comprising a rotatable pinhole body.

The adjoining of a rotatable pinhole body to adjacent elements, preferably plate-shaped elements, of the collimator is preferably configured such that undesired penetration of gamma radiation is prevented. For example, an edge of a collimator element adjacent to the pinhole body is configured with an essentially C-shaped cross-section, wherein the pinhole lies partially in the opening of the C shape.

In suitable embodiments of the invention, it is possible to adjust a focus volume—that is defined by the overlap of the fields of view of the pinholes of the collimator—with respect to the position and/or size thereof by rotating the one or more pinhole bodies of the collimator.

In suitable embodiments of the invention, it is possible to adjust the focus volume with respect to the position and/or size thereof by rotating the one or more pinhole bodies of the collimator without moving the object carrier and object carried by said carrier. In a practical embodiment, for example, a person can remain lying on an object carrier configured as a bed, wherein the bed remains stationary, while by rotating the one or more pinhole bodies of the collimator (among other means), the focus volume with respect to the position and/or size thereof is adjusted and/or varied with respect to the person who is kept stationary. In this manner, for example, an unpleasant experience on the part of the person is alleviated or prevented.

In embodiments, it is possible without rotating the collimator around the longitudinal direction of the object space to set the focus volume with respect to position and/or size.

In suitable embodiments, it is possible by rotating the one or more pinhole bodies of the collimator to selectively open and close pinholes of the collimator.

In suitable embodiments, the pinholes in the one or more rotatable pinhole bodies are the only pinholes of the collimator, i.e., no pinholes are then provided in other collimator elements. For example, the other collimator elements are flat or curved blocks or plates of collimator material, for example tungsten. In another embodiment, one or more pinholes are indeed provided in the one or more other collimator elements, for example one or more rows of pinholes parallel to the longitudinal direction. For example, for one or more pinholes, or one or more rows of pinholes, in the one or more other collimator elements, pinhole shutter devices are provided for selectively opening and closing the pinholes.

In suitable embodiments, the SPECT scanner, particularly the collimator thereof, is operated and/or configured such that that the projections on the one or more detectors of the pinholes belonging to different rotatable pinhole bodies do not overlap one another or do so to the least extent possible.

In suitable embodiments, the collimator is configured to be placed in and removed from the SPECT scanner as a unit, wherein the detection device does not constitute a part of the exchangeable collimator unit.

In suitable embodiments, the detection device is configured with one or more detectors that form a closed loop around the imaging space and around the collimator, which is preferably configured as a closed loop.

Preferably, the one or more detectors is/are mounted as a fixed, not easily exchangeable component of the SPECT scanner, and the collimator, as a unit or in one or more parts, is mounted as an easily exchangeable component of the SPECT scanner.

Preferably, the one or more detectors is/are mounted as a permanent component of the SPECT scanner, wherein the one or more detectors is/are rotatable around the longitudinal direction of the imaging space, preferably over a limited angle of rotation, for example an angle that is less than 90°. Optionally, the one or more detectors is/are rotatable over a limited angle of rotation around the longitudinal direction and the collimator is likewise rotatable over a limited angle of rotation around the longitudinal direction, e.g. the rotational movements are synchronous, for example for placing both the collimator and the detectors in another position with respect to the object. For example, the limited rotation over an angle is less than 90°, for example +20° and −20° with respect to a standard position.

Preferably, the one or more detectors are mounted as a permanent component of the SPECT scanner, wherein the one or more detectors form(s) a detection surface with a fixed, non-adaptable cross-section around the imaging space and the collimator.

For example, a mobile cart is provided that carries the collimator and by means of which the collimator is to be placed in and removed from the SPECT scanner as an exchangeable unit.

In suitable embodiments, one or more of the rotatable pinhole bodies is/are provided with one or more pinhole clusters comprising clustered pinholes. As mentioned above, it can be provided that a pinhole shutter device is present for selectively opening and closing at least one pinhole of a cluster, e.g. all pinholes of a cluster or of multiple clusters. For example, a shutter is provided that is arranged on the side of the rotatable pinhole body facing away from the imaging space. Alternatively, the invention also provides the selective opening and closing of one or more pinholes and/or one or more pinhole clusters, specifically by rotating the corresponding rotatable pinhole body, with the result that in an effective or active position of the pinhole body, the one or more pinholes or pinhole clusters is/are open, and in a closed or blocked position, the one or more pinholes or pinhole clusters is/are closed.

In suitable embodiments, each of one or more of the rotatable pinhole bodies is provided with one or more pinhole clusters comprising clustered pinholes. The invention makes it possible, instead of the stepwise adjustment of the prior art, to smoothly adjust the focus volume with respect to position and size without rotating the entire collimator, and thus for example to do so in a manner optimally tailored to the size of the object to be scanned and/or the part thereof to be examined. This makes selection of the position of the focus volume more accurate and flexible, with the result that maximum sensitivity and improved sampling can be achieved.

The rotation of a pinhole body in the collimator, i.e. with respect to a collimator body wherein the pinhole body is arranged or with respect to adjacent collimator elements if the pinhole body is arranged between them, can be made possible in any desired manner. For example, rotation can be effected by manual rotation or manually with an external tool or with an actuator belonging to the collimator and/or the scanner, for example with an electromotor or another motor. It is possible to provide an individual actuator for each rotatable pinhole body, or several, optionally all, rotatable pinhole bodies are coupled via a transmission with a joint actuator. For example, the rotation of the one or more rotatable pinhole bodies is fully automated based on a previously set movement pattern.

In an embodiment, a rotatable pinhole body essentially spherical and to be rotated around more than one axis of rotation.

In a preferred embodiment, a rotatable pinhole body is elongated and to be exclusively rotated about an axis of rotation parallel to the longitudinal direction. For example, the pinhole body is rotationally symmetrical around the axis of rotation, e.g. the pinhole body is an essentially cylindrical pinhole body with a solid cross-section with one or more pinholes therein.

In a preferred embodiment, the axis of rotation of the pinhole body, and preferably of all rotatable pinhole bodies of the collimator, extends essentially parallel to said longitudinal direction. This provides the possibility of moving, i.e. "sweeping", the part of the object space seen through the relevant pinhole(s) through the same object space in a direction that is transverse to said longitudinal direction. The angle of rotation of a pinhole body during this movement is, preferably, e.g. between 5 and 25° with respect to the radial direction in both or all sweeping directions.

In embodiments of a rotatable pinhole body, respective main pass-through directions of two or more pinholes of said body approach one another in the object space, wherein the respective fields of view of said two or more pinholes together form the scan volume. In a central position, the fields of view overlap one another in a focus volume. By rotating the pinholes, the fields of view also move through the object space and can therefore enlarge the scan volume. All data collected in the scan volume can be used in reconstruction of the distribution of the radionuclide(s). It is to be noted that the pinholes all preferably rotate in the same direction so that any overlap on the detector remains limited.

In embodiments, said set of pinholes of the collimator comprises two or more sub-sets of multiple pinholes each, wherein in each of these sub-sets, all of the pinholes are arranged in a pinhole body that is rotatable about a respective axis of rotation parallel to the longitudinal direction. This makes it possible, in a simple and efficient manner, to move a focus volume, i.e. a volume that is simultaneously covered by two or more pinholes, with respect to the object space, in particular in a plane perpendicular to the longitudinal direction. An example of such a pinhole body comprises multiple pinholes in a row, for example in a row in a cylindrical pinhole body. For example, these pinholes then have respective pass-through directions that are directed towards one another, and advantageously focussed on one point.

In embodiments, said set comprises one or more first pinholes with one or more first properties, and also one or more second pinholes with one or more other, second properties, wherein the first and second properties are preferably selected from a sensitivity, in particular a pass-through surface of the pinhole, and/or a main pass-through direction, and/or an acceptance angle. In this manner, the rotatability of the pinhole bodies makes it possible in a simple manner to quite rapidly modify one or more important properties of the collimator. Some specific examples are described below, but other embodiments and combinations are also possible.

In embodiments, the acceptance angle of the first pinholes is configured to be greater than that of the second pinholes. This influences for example the dimensions and optionally the position of a focus volume that is seen by two or more pinholes. Even more important, is that with a smaller acceptance angle, the image sharpness becomes better at higher gamma energies. For this reason, this collimator can be made better suited for such higher gamma-energies by rotating the relevant second pinholes into an active position and the first pinholes, which can be in another orientation in the same pinhole body or in a completely different pinhole body than the second pinholes, into an inactive position. It may then be necessary to provide more of such low acceptance angle pinholes in comparison with the (relatively) high acceptance angle pinholes. It is to be noted that in such a case, more pinholes are advantageously provided both in the longitudinal direction of the collimator and preferably also along the perimeter of the collimator. The latter can be achieved, for example, by providing, seen in a circumferential direction of the collimator, more pinhole bodies with pinholes having a first, relatively lower acceptance angle than pinhole bodies having a second, relatively higher acceptance angle. Examples of different acceptance angles are for example between 15 and 20° for a small acceptance angle and between 20 and 50° for a large acceptance angle, but other values are not excluded. A further possibility for this measure will be explained in greater detail below.

Instead of individual pinholes, it is also possible to provide a cluster of pinholes, such as disclosed for example in EP2073039 from the same applicant. Each cluster of pinholes can then serve as a (second) pinhole, but can handle higher particle energies because a smaller opening angle is provided per sub-pinhole in the cluster so that less edge penetration occurs.

For example, as in EP2073039, the collimator comprises multiple pinhole clusters, wherein each pinhole cluster comprises multiple pinholes with mutually non-parallel central lines that are at a mutual distance that is smaller than a distance between one of the at least two pinholes of said pinhole cluster on the one hand and any pinhole from any other pinhole cluster on the other, and with a pinhole cluster field of view that is composed of the fields of view of the multiple pinholes of the pinhole cluster, wherein in the collimator, all pinhole clusters are designed and configured such that a mutual overlap of their pinhole cluster fields of view is determined, wherein said overlap defines a focus volume that is seen through all pinhole clusters, and wherein at least one pinhole cluster is designed and configured such that for at least one, and preferably each of the pinholes of said pinhole cluster, a part of the focus volume is outside the field of view of said pinholes.

In embodiments, the first pinholes comprise mutually parallel main pass-through directions, and the second pinholes comprises main pass-through directions mutually focused on one point.

In an embodiment, the first and second pinholes are arranged in one individual pinhole body, for example each first pinhole close to axial ends of the pinhole body and multiple second pinholes in between.

For example, the first and second pinholes lie in a row in the pinhole body essentially in a common plane, or for example the first and second pinholes lie in corresponding first and second planes that, seen in the direction of the axis of rotation of the pinhole body, form an angle with respect to each other.

For example, the pass-through directions of the first pinholes are essentially radially aligned, i.e. for example at right angles to said longitudinal direction. The first pinholes thus cover a relatively large volume of the object space, so that scanning of an object can take place rapidly without having to displace the object in an undesired manner through the object space. The second pinholes then preferably have pass-through directions that run toward each other axially (seen in a longitudinal direction) and thus cover a smaller volume, but because that volume, the focus volume, is viewed axially from more directions, the volume is scanned with greater sensitivity.

In a suitable embodiment, the scan property of the collimator can be adjusted by rotating the one or more rotatable pinhole bodies of the collimator, possibly within a very short period of time. For example, a rapid scan can be carried out with said first pinholes in an active position, for example in order to determine where the region of interest is located in the object. By then rotating the one or more pinhole bodies until said second pinholes are active, it becomes possible to carry out a more sensitive, longer-lasting scan of the region of interest.

In embodiments, the respective fields of view of all pinholes of at least two, and in particular of all sub-sets, overlap one another in the object space, in particular in a focus volume in the object space. This provides an effect comparable to that described above for individual (sub-sets of) pinholes, i.e. the focus volume is viewed through multiple sets of pinholes, so that even more (photon) data is collected and the scan is more accurate.

For example, said set and/or said sub-set of at least one pinhole body comprises one or more first pinholes with a first sensitivity and/or resolution and a first main pass-through direction, and also comprises one or more second pinholes with a second, lower sensitivity but higher resolution, as well as a second main pass-through direction, wherein preferably the respective perpendicular projections of the first main pass-through direction and the second main pass-through direction on a plane perpendicular to the axis of rotation of the pinhole body mutually include an angle of at least 60°, and more preferably essentially 90°.

Said first and second pinholes are preferably close to each other, such as with a centre-to-centre distance equal to a thickness of the collimator material, but other distances are possible. This embodiment makes it e.g. possible to carry out a relatively rapid overview scan ("scout scan") with the high-sensitivity pinholes in order to determine the region(s) of interest in this manner. After rotation of a suitably configured pinhole body such that the high-sensitivity, low-resolution pinholes are rotated away and the lower-sensitivity, higher-resolution pinholes are rotated into an active position, a scan can efficiently be carried out of said region(s) of interest.

The result is that the total scan does not have to last as long. For example, pinholes with a higher sensitivity have a greater net pass-through area.

In embodiments, one or more pinhole bodies comprise a combination or two or more types of pinholes, such as focused pinholes and/or parallel pinholes, each with a first sensitivity or a second sensitivity, optionally a third sensitivity, and/or each with a first acceptance angle or another, second acceptance angle.

It is noted that the different pinholes per pinhole body can herein be rotatable as a whole, but can also be orientable as a group as described above by selecting the rotation angle other than said included angle.

In embodiments, at least one, and preferably each, pinhole body is configured to be rotationally symmetrical, for example cylindrical, around the axis of rotation. Of course, a cylindrical body is particularly suitable for rotation in the material of a collimator.

In a possible embodiment, the rotatable pinhole body has an essentially circular segment-shaped cross-section with an essentially flat first side and a circular arc-shaped second side, wherein the at least one pinhole extends from a first opening on the essentially flat first side of the pinhole body to a second opening on a second side of the pinhole body located opposite the first side.

For example, the smallest cross-sectional part of the pinhole is located farther from the first side than the distance to the second side of the rotatable pinhole body.

For example, the smallest cross-sectional part of the pinhole is located farther from the essentially flat first side than the distance to the circular arc-shaped side of the rotatable pinhole body.

In an embodiment, the collimator is provided with at least one rotatable pinhole body with at least one pinhole therein, which pinhole body is arranged rotatably around an axis of rotation between adjacent collimator elements, wherein the at least one pinhole extends from a first opening on a first side of the pinhole body to a second opening on a second side of the pinhole body located opposite the first side, wherein each of the collimator elements has an object space side and a detector side that respectively are adjacent to the object space and are turned toward the detector, between which object space side and detector side a thickness of the collimator elements is defined, as well as an imaginary centre plane through the centre of the thickness, wherein the axis of rotation of the pinhole body is located at a distance away from the centre planes of the adjacent collimator elements. By means of this geometry, a number of advantages can be achieved with respect to the effective size of the object space, variation in distance between an object and a smallest cross-sectional part of a pinhole, etc.

For example, it is provided that the smallest cross-sectional part, seen in the direction between the first opening and the second opening of the pinhole, is located at a distance from the axis of rotation of the pinhole body, such that—during use—the distance between the smallest cross-sectional part of the pinhole and an object positioned by the object carrier is variable by selectively rotating the pinhole body with the first side thereof or the second side thereof toward the object space.

In a possible embodiment, the pinhole body is configured such that the first side, which for example can be essentially flat, is at a smaller distance from the axis of rotation than the second side, which for example can be circular arc-shaped.

Preferably, each rotatable pinhole body extending in a longitudinal direction is elongated and at least as long, and possibly even longer, than the collimator length of the adjacent collimator elements, seen in the longitudinal direction. This makes it easy to engage on the pinhole body in order to rotate it, for example on an axial end of a rotatable pinhole body, for example with a toothed wheel or the like or directly with an actuator. Nevertheless, it is also possible to provide shorter pinhole bodies. For example, multiple rotatable pinhole bodies can be arranged successively in a longitudinal direction, for example a pair of pinhole bodies, for example wherein the one pinhole body is arranged from the one axial end in a slot and the other is arranged from the other axial end in the slot.

The collimator can be provided, as is customary, at both axial ends with side-shielding collimator elements. It can be advantageous to configure a rotatable pinhole body with a length such that it falls in its entirety within a (side) shielding of the collimator.

In embodiments, the SPECT scanner further comprises a pinhole body rotation device for rotating one or more of the pinhole bodies about the respective axis of rotation, as well as a control unit for controlling the pinhole body rotation device. It is described above that the pinhole bodies in principle could be rotatable by hand or with an external tool held in the hand.

It will be apparent that it is advantageous to provide a pinhole body rotation device in the scanner, optionally as a unit with the collimator, that can carry out said rotation under the control of a control unit. This improves the repeatability and reduces the change of errors. Such a pinhole body rotation device can be construed in a simple manner, with any mechanical drive and transmission to one or multiple, optionally all, pinhole bodies.

It is possible to configure the control unit and the pinhole body rotation device for mutually coordinated rotation of several of the pinhole bodies such that the respective fields of view of the pinholes are displaceable within the object space. By coupling the drive of respective pinhole bodies with suitable, for example fixed, transmissions, it is easily possible to coordinate and/or synchronize these movements and thus to maintain an optimum focus volume. It is also possible to configure the pinhole body rotation device and the control unit such that pinhole bodies of the collimator can be rotated independently of one another, e.g. an individual drive is provided for each pinhole body.

In advantageous embodiments, the collimator has an adjustable cross-section perpendicular to the longitudinal direction. A collimator is thus provided with a modifiable cross-section, which for example can provide space for objects of different sizes or cross-sections, for example for an adult and a child. Moreover, the possibility is provided of allowing the pinholes of the collimator to form images at different distances from the object. Because of the different distances from the object, measurements can be conducted with a different imaging scale, optionally resolution, and optionally sensitivity. This therefore provides a highly flexible collimator and SPECT scanner.

There are no particular limitations on the measures allowing to achieve the collimator having an adjustable cross-section. For example, a design can be used in which a collimator is formed by four blocks as collimator elements that are displaceable independently from one another. With mutual shifting of the blocks, the result is a collimator having a rectangular cross-section with adjustable dimensions. Each of the individual blocks can be provided with one or more of said rotatable pinhole bodies so that the pinholes can be oriented, e.g. because the pinholes themselves will shift with respect to the object due to shifting of the blocks, or when another object is examined, for example a larger or smaller object.

In an advantageous embodiment, the collimator comprises multiple collimator elements arranged in a series that extends, seen in a circumferential direction of the collimator, at least partially around the longitudinal direction of the imaging space, wherein adjacent collimator elements of the series are pivotable with respect to one another. For example, adjacent collimator elements are interconnected by a pivot mechanism that forms a pivot axis running parallel to said longitudinal direction. Preferably, one rotatable pinhole body is always arranged between adjacent collimator elements of the series, which pinhole body is rotatable with respect to the adjacent collimator elements around an axis of rotation that extends essentially parallel to said longitudinal direction and preferably coincides with the pivot axis. Preferably, the cross-section of the collimator is adjustable perpendicularly to the longitudinal direction by pivoting the collimator elements.

The embodiment of the collimator with a series of pivotable collimator elements, for example in a closed loop around the imaging space, allows for a collimator with a changeable cross-section possible that can provide space for objects of different size or cross-section and can then be adapted to said objects with respect to the cross-section, for example by positioning the pinholes for a scan as close as possible to the object. Moreover, the possibility is also provided of allowing pinholes to form images at different distances from the object, for example by pivoting the collimator elements and thus moving the elements. Additionally or alternatively, it is possible in a suitable embodiment to rotate the pinholes, which may be located at the position of the pivot lines at a first distance from the object, from a first angle position (either pass-through or blocking) to the other angle position, and conversely, to rotate the pinholes located at a second distance from the object from the other angle position (either pass-through or blocking) to the first position. The different distance from the object makes it possible to conduct measurements with a different imaging scale, optionally resolution, and optionally sensitivity. This therefore provides a highly flexible collimator and SPECT scanner.

It is also possible to provide, at the site of first pivot lines between adjacent collimator elements, which first pivot lines can be located at a relatively short distance from the centre of the object space, pinhole bodies having both multiple first pinholes with a first, relatively small acceptance angle and multiple second pinholes that are arranged with respect to the first pinholes over an angle that is rotated about the axis of rotation of the pinhole body and have a second, greater acceptance angle. In this case, if desired, it is possible to provide pinhole bodies having multiple of said second pinholes at the site of second pivot lines that can be located at a relatively greater distance as compared to the first pivot lines from the centre of the object space. These embodiments can be useful in that in a first condition of the collimator, wherein the first pivot lines are actually closer to the centre of the object space, the first pinholes of the corresponding pinhole bodies are open and the (wider) second pinholes are therefore rotated and closed, while the pinholes in the pivot lines that are then located farther away from the centre of the object space are then closed. The result is a collimator with the first pinholes having a small acceptance angle at a short distance from the object. In a second condition, wherein the collimator is enlarged by pivoting the collimator elements, it is to be possible to bring the first and second pivot lines to essentially the same distance from the centre of the object space. In this case, in all of the pinhole bodies, the second pinholes having a greater acceptance angle can be rotated into the open position. This results in a collimator with effectively more pinholes, at a greater distance, and with a greater acceptance angle. It is therefore possible, using the same collimator, to continue using a very large portion of the detector surface without (much) overlap, while the other imaging properties (other resolution, higher gamma energy possible without blur) can provide useful information on the object.

For example, the collimator elements are embodied as plate-shaped, for example as a flat block, or circular arc-shaped. In the former case, the collimator will then have in a first configuration e.g. a pointed star-shaped cross-section, and in another second configuration with the largest cross-section, a polygonal cross-section, optionally with one or more intervening states, which in general will also have a star shape, but less pointed. In the second case with the circular arc-shaped elements, the collimator can in a first configuration have a small cross-section with a star shape having rounded star points, and in a second, largest configuration, have an essentially circular cross-section, so that the collimator in this configuration can accommodate the largest object and can then optionally rotate around the object, for example over an angle range of less than one rotation, for example less than a quarter rotation. Moreover, this does not exclude other elements and shapes of the collimator.

It is to be noted that all other measures and advantages mentioned in this application are in principle fully applicable, such as rotating the pinholes and thus moving a focus and/or scan volume through the object space.

Furthermore, in embodiments with collimator elements, collimator element displacement devices are also provided, and the control unit is configured for mutually coordinated control of the displacement devices in order to change the shape of the collimator. The results can then be as described above, but in this case without requiring manual operation by a human operator.

In embodiments, the SPECT scanner further comprises a displacement device for displacing the object carrier in the object space, for example along said longitudinal direction. The movement through the object space of the object carrier, which is common per se, such as moving a bed for a patient in a longitudinal direction, can make it possible, in combination with the scan volume that is displaceable through the object space by rotating the pinhole bodies, to scan each part of the patient with high sensitivity and resolution, e.g. in a spiral-shaped relative movement. The object carrier does not have to perform any complex movement, nor is it necessary for the collimator or scanner to be displaced as a whole, because it is possible to rotate only the much lighter pinhole bodies. This results in much less discomfort for the patient during scanning and greater flexibility in the SPECT scanner.

In using the scanner, one can first make an image reconstruction system matrix for each position of the pinholes, for example using a point source and special software in a manner known per se. Because of the many possibilities offered by such a collimator/scanner, this is a somewhat time-consuming task, but it only has to be carried out once for each type of collimator. Using the matrices of all of the configurations of the pinholes and for each of the bed positions, the 3D radionuclide distribution can then be optimally reconstructed.

The invention also relates to a collimator for a SPECT scanner. In general, it relates to a SPECT scanner collimator that is configured for use in a SPECT scanner, for example a SPECT scanner such as explained herein, wherein the collimator is configured to extend at least partially around an object space of the SPECT scanner, which object space comprises a longitudinal direction, wherein the collimator comprises a set of multiple pinholes each of which comprises a field of view with a main pass-through direction for gamma radiation, wherein the collimator is provided with at least one rotatable pinhole body with at least one pinhole therein, which pinhole body is arranged in the collimator rotatably around at least one corresponding axis of rotation.

In an embodiment, the pinhole body is rotatably arranged in the collimator exclusively about an axis of rotation that extends essentially parallel to said longitudinal direction.

All other features that are mentioned in embodiments of the SPECT scanner can in principle be combined with such a collimator, and the corresponding aspects and advantages are then also applicable to (the use of) such a collimator. For this reason, they will not be repeated in the interest of brevity.

The advantage of such a separate collimator is that it can replace the collimator of an existing SPECT scanner, so that the thus reconfigured SPECT scanner takes on the features of this invention.

The invention further relates to a system comprising the collimator according to the invention in combination with a detection device with one or more detectors for detecting gamma radiation that is allowed to pass from the object space by pinholes of the collimator. Furthermore, the features mentioned for the SPECT scanner according to the invention as optional details can also be applied to this combination, and the corresponding advantages can also be applied to the combination.

The advantage of such a combination of a collimator and detection device is that this combination can relatively easily be arranged in an existing scanner, so that the functionality or flexibility of the scanner is enhanced by the aspects described for the present invention. It is to be noted that in principle, the existing scanner does not even have to be a SPECT scanner.

It is further to be noted that supplementary measures can be provided. Examples thereof are measures known per se, such as the provision of shielding between the (acceptance angles of the) pinholes. The collimator can also be arranged to be rotatable as a whole, optionally provided with a collimator rotation device. This allows the collimator to be rotatable with respect to the object and/or the material world. Even more angle data can therefore be collected with respect to the object. Moreover, the collimator does not need to be rotated over 360°, but 360°/(number of pinholes positioned in a ring around the object) is sufficient in order to make the collimator rotatable. In other words, if there are four pinholes around the object space, rotation over 90°, and in practice, usually an angle somewhat smaller than 90° in a few steps, is sufficient. Of course, several such rings, whether or not focused, can be provided successively.

Furthermore, frame devices can be provided for limiting and defining the projections of the object space on the detector(s) via the pinholes. For example, such frame devices, such as plates with optionally adjustable openings, are configured to allow adjacent projections to overlap on the detector surface to a maximum of 20%, and in some embodiments not at all. Details on such frame devices are described in WO2007/105942, among other documents.

A shutter device can also be provided that is configured to close of one or more pinholes in a controlled manner, i.e. to make them impenetrable for radiation, by placing a flap or the like in front of or in them. The shutter device is preferably controllable by means of the control unit. It is to be noted that it can be advantageous to configure each pinhole body such that it can be completely closed by rotating it to a suitable position. Each pinhole body can therefore be shut.

In an embodiment, a pinhole body that is elongated and rotatable around one axis of rotation is provided with a recess extending over at least a part of the length thereof, wherein the field of view of at least one pinhole, preferably of a group of pinholes, extends through the recess, and wherein a shutter element fitting into the recess is provided that is configured, in an active position thereof, to block the field of view of the at least one pinhole. For example, the recess is present inside the pinhole body or in the perimeter of the pinhole body, for example as an elongated internal channel or as an elongated groove in the outside of the pinhole body. For example, the shutter element comprises holes corresponding to the location of the one or more pinholes, and the shutter element is linearly displaceable between an opened position of the pinhole(s) wherein the one or more holes is/are aligned with the one or more pinholes, for example, the holes form a part of the pinhole other than the part with the smallest passage, and a closed position wherein a radiation-impermeable part of the shutter element blocks the pinhole from allowing radiation to pass through. Optionally, the one or more holes in the shutter element is/are filled with a radiation-permeable material.

The first aspect of the invention also relates to a SPECT scanner for making images of an object using gamma radiation, comprising:

an object space with a longitudinal direction, an object carrier configured for bringing an object into the object space in said longitudinal direction and for positioning the object in the object space, a collimator that extends at least partially around the object space, wherein the collimator comprises a set of multiple pinholes each of which comprises a field of view with a main pass-through direction for the gamma radiation, a detection device with at least one detector configured for detecting gamma radiation that is allowed to pass through from the object space by one or more of the pinholes, wherein the collimator is provided between the object space and the at least one detector, wherein the collimator is provided with at least one rotatable pinhole body with at least one pinhole therein, which pinhole body is rotatably arranged in the collimator around an axis of rotation, for example between adjacent collimator elements, further comprising a pinhole body rotation device that is configured for rotating the pinhole body around the axis of rotation, and wherein the at least one pinhole extends from a first opening on a first side of the pinhole body to a second opening on a second side of the pinhole body located opposite the first side, wherein the at least one pinhole has a smallest cross-sectional part that defines the smallest cross-section for gamma radiation of the pinhole and is located at a distance from the first opening and from the second opening of the pinhole, wherein the smallest cross-sectional part, seen in the direction between the first opening and the second opening of the pinhole, is located at a distance from the axis of rotation of the pinhole body, such that—during use—the distance between the smallest cross-sectional part of the pinhole and an object positioned by the object carrier is variable by selectively rotating the pinhole body with the first side thereof or the second side thereof toward the object space. This solution can, for example, be applied in a collimator wherein the adjacent collimator elements together have a fixed, non-adjustable geometry, for example a cross-sectionally polygonal collimator around the object space with fixed dimensions. For example, a rotatable pinhole body with an axis of rotation parallel to the corners of the polygonal collimator can then be attached to one or more corners of the polygonal cross-section and/or in one or more of the walls of the polygonal cross-section. By selectively rotating the pinhole body or several, optionally all of the rotatable pinhole bodies, the imaging properties of the collimator can then be varied. The method of variation is also to be combined with an embodiment of the collimator having an adjustable cross-sectional shape, for example such as further explained herein.

In an embodiment, the variation of the distance between the smallest cross-sectional part of the pinhole and an object positioned by the object carrier effected by selectively rotating the pinhole body with the first side thereof or the second side thereof toward the object space is at least 10 mm.

In an embodiment, each of the adjacent collimator elements has an object space side and a detector side, which respectively are adjacent to the object space and face toward the detector, between which object space side and detector side a thickness of the collimator elements is defined.

In an embodiment, the pinhole body has a diameter that is larger than a thickness of the adjacent collimator elements between the object space side and the detector side thereof.

In an embodiment, the first side of the pinhole body is at a smaller distance from the axis of rotation than the second side.

In an embodiment, the first side, in which the first opening of the at least one pinhole is located, is an essentially flat first side. Optionally, the first side shows a slight curvature. It is also possible for the second side to have an essentially flat configuration.

In a practical embodiment, the pinhole body has an essentially circular segment-shaped cross-section with an essentially flat first side and a circular arc-shaped second side, wherein the at least one pinhole extends from a first opening on the essentially flat first side of the pinhole body to a second opening on a second side of the pinhole body located opposite the first side.

In an embodiment, the smallest cross-sectional part of the pinhole is farther from the first side than the distance to the second side. For example, the smallest cross-sectional part of the pinhole is farther from the essentially flat first side than the distance to the circular arc-shaped side.

The first aspect of the invention also relates to a SPECT scanner for making images of an object using gamma radiation, comprising:
- an object space with a longitudinal direction,
- an object carrier configured for bringing an object into the object space in said longitudinal direction and for positioning the object in the object space,
- a collimator that extends at least partially around the object space, wherein the collimator comprises a set of multiple pinholes each of which comprises a field of view with a main pass-through direction for the gamma radiation,
- a detection device with at least one detector configured for detecting gamma radiation that is allowed to pass through from the object space by one or more of the pinholes, wherein the collimator is provided between the object space and the at least one detector,
- wherein the collimator is provided with at least one rotatable pinhole body with at least one pinhole therein, which pinhole body is rotatably arranged around an axis of rotation between adjacent collimator elements,
- further comprising a pinhole body rotation device that is configured for rotating the pinhole body around the axis of rotation,
- and wherein the at least one pinhole extends from a first opening on a first side of the pinhole body to a second opening on a second side of the pinhole body located opposite the first side,
- wherein the at least one pinhole has a smallest cross-sectional part that defines the smallest cross-section for gamma radiation of the pinhole and is located at a distance from the first opening and the second opening of the pinhole,
- wherein each of the collimator elements has an object space side and a detector side that respectively are adjacent to the object space and face toward the detector, between which object space side and detector side a thickness of the collimator elements is defined.

In an embodiment, the pinhole body has a diameter that is larger than a thickness of the adjacent collimator elements between the object space side and the detector side thereof.

In an embodiment, the first side of the pinhole body has a smaller distance to the axis of rotation than the second side.

In an embodiment, the first side, where the first opening of the at least one pinhole is located, is an essentially flat first side. Optionally, the first side shows a slight curvature. It is also possible for the second side to have an essentially flat configuration.

In a practical embodiment, the pinhole body has an essentially circular segment-shaped cross-section with an essentially flat first side and a circular arc-shaped second side, wherein the at least one pinhole extends from a first opening on the essentially flat first side of the pinhole body to a second opening on a second side of the pinhole body located opposite the first side.

In an embodiment, the smallest cross-sectional part of the pinhole is located farther from the first side than the distance to the second side. For example, the smallest cross-sectional part of the pinhole is located farther from the essentially flat first side than the distance to the circular arc-shaped side.

A second aspect of the invention relates to a SPECT scanner for making images of an object using gamma radiation, comprising:
- an object space with a longitudinal direction,
- an object carrier configured for bringing an object into the object space in said longitudinal direction and for positioning the object in the object space,
- a collimator that extends at least partially around the object space, wherein the collimator comprises a set of multiple pinholes each of which comprises a field of view with a main pass-through direction for the gamma radiation,
- a detection device with at least one detector configured for detecting gamma radiation that is allowed to pass through from the object space by one or more of the pinholes, wherein the collimator is provided between the object space and the at least one detector, wherein the collimator comprises multiple collimator elements arranged in a series which, seen in a circumferential direction of the collimator, extends at least partially around the longitudinal direction of the imaging space, wherein adjacent collimator elements of the series are pivotable with respect to one another, for example are interconnected by a pivot mechanism that forms a pivot axis running parallel to said longitudinal direction.

Preferably, in the second aspect of the invention, each pinhole body as described herein is arranged between adjacent collimator elements of the series, which pinhole body is rotatable with respect to the adjacent collimator elements around an axis of rotation that extends essentially parallel to said longitudinal direction. In combination with a rotatable pinhole body arranged between adjacent collimator elements, or as an alternative arrangement, a rotatable pinhole body can also be arranged in a collimator element, i.e. at a distance from the pivot lines of that element. In a practical embodiment, a pivot axis between adjacent collimator elements coincides with the axis of rotation of a rotatable pinhole body.

Preferably, in the second aspect of the invention, the cross-section of the collimator perpendicular to the longitudinal direction is adjustable by pivoting the collimator elements.

For example, the collimator of the second aspect of the invention is adjustable to an essentially round cross-sectional shape and to one or more of an essentially oval cross-sectional shape and a pointed cross-sectional shape.

Preferably, in the second aspect of the invention, a displacement device is further provided for displacing the object carrier at least in said longitudinal direction in order to bring an object carried by the object carrier into and out of the object space, preferably in said longitudinal direction in a horizontal plane, optionally also in a lateral direction transverse to the longitudinal direction in said horizontal plane.

Preferably, in the second aspect of the invention, the object carrier is configured for carrying a person in a lying position, and wherein the scanner is configured for imaging a part of the person, for example of the head or another part of the body, for example the torso or a part of the torso.

Preferably, in the second aspect of the invention, the collimator is configured in the form of a closed loop that extends completely around the object space.

Preferably, in the second aspect of the invention, the collimator comprises at least four, preferably at least eight, collimator elements arranged in a series that extends around the longitudinal direction of the imaging space seen in a circumferential direction of the collimator, wherein adjacent collimator elements of the series are pivotable with respect to one another, for example are interconnected by a pivot mechanism that forms a pivot axis running parallel to said longitudinal direction, wherein preferably, one pinhole body each is arranged between adjacent collimator elements of the series, which pinhole body is rotatable with respect to the adjacent collimator elements around an axis of rotation that extends essentially parallel to said longitudinal direction, and wherein preferably, the cross-section of the collimator perpendicular to the longitudinal direction is adjustable by pivoting the collimator elements. In a practical embodiment, a pivot axis between adjacent collimator elements coincides with the axis of rotation of a rotatable pinhole body.

Preferably, in the second aspect of the invention, one or more of the collimator elements is/are adjustable in width seen in the circumferential direction, for example, one or more of the collimator elements each comprise(s) a first sub-element and a second sub-element that at least partially overlap each other and are displaceable with respect to each other such that the width of the collimator element is adjustable, for example wherein one or more actuators is/are provided that are configured for adjusting the width of one or more of the collimator elements.

The second aspect of the invention also relates to a SPECT scanner collimator that is configured to extend at least partially around an object space, wherein the collimator comprises a set of multiple pinholes each of which comprises a field of view with a main pass-through direction for gamma radiation, wherein the collimator comprises multiple collimator elements arranged in a series which, seen in a circumferential direction of the collimator, extend at least partially around the longitudinal direction of the imaging space, wherein adjacent collimator elements of the series are pivotable with respect to one another, for example are interconnected by a pivot mechanism that forms a pivot axis running parallel to said longitudinal direction.

The collimator of the second aspect of the invention can have one or more of the features described herein of the SPECT scanner according to the second aspect of the invention.

It is to be clear that the SPECT scanner and/or collimator according to the second aspect of the invention can have one or more of the features of the SPECT scanner and/or collimator according to the first aspect.

The second aspect of the invention also relates to a system comprising a SPECT scanner collimator and a detection device for detecting gamma radiation that is allowed to pass through from the object space by pinholes of the SPECT scanner collimator.

The invention also relates to a method for adjusting an imaging device of a SPECT scanner or a SPECT scanner collimator such as described herein, wherein the at least one rotatable pinhole body with at least one pinhole therein, said pinhole body being rotatably arranged in the collimator around at least one corresponding axis of rotation, is rotated around the axis of rotation.

The invention also relates to a method for adjusting an imaging device of a SPECT scanner or a SPECT scanner collimator such as described herein, wherein adjacent collimator elements are pivoted with respect to one another in order to change the cross-sectional shape of the collimator.

The invention will be explained in the following by means of several non-limitative embodiments, as well as the drawing.

BRIEF DESCRIPTION OF THE DRAWINGS

In the drawings the figures show the following:

FIGS. 12*a, b* are schematic sectional views of an alternative collimator according to the invention with the rotatable pinhole body in a first (FIG. 12*a*) and second (FIG. 12*b*) position;

FIG. 13*a, b* are schematic sectional views of a rotatable pinhole body according to FIGS. 12*a, b* in a loop-shaped collimator, in the first position (FIG. 13*a*) and in the second position (FIG. 13*b*);

DETAILED DESCRIPTION OF EMBODIMENTS

Figure 1:
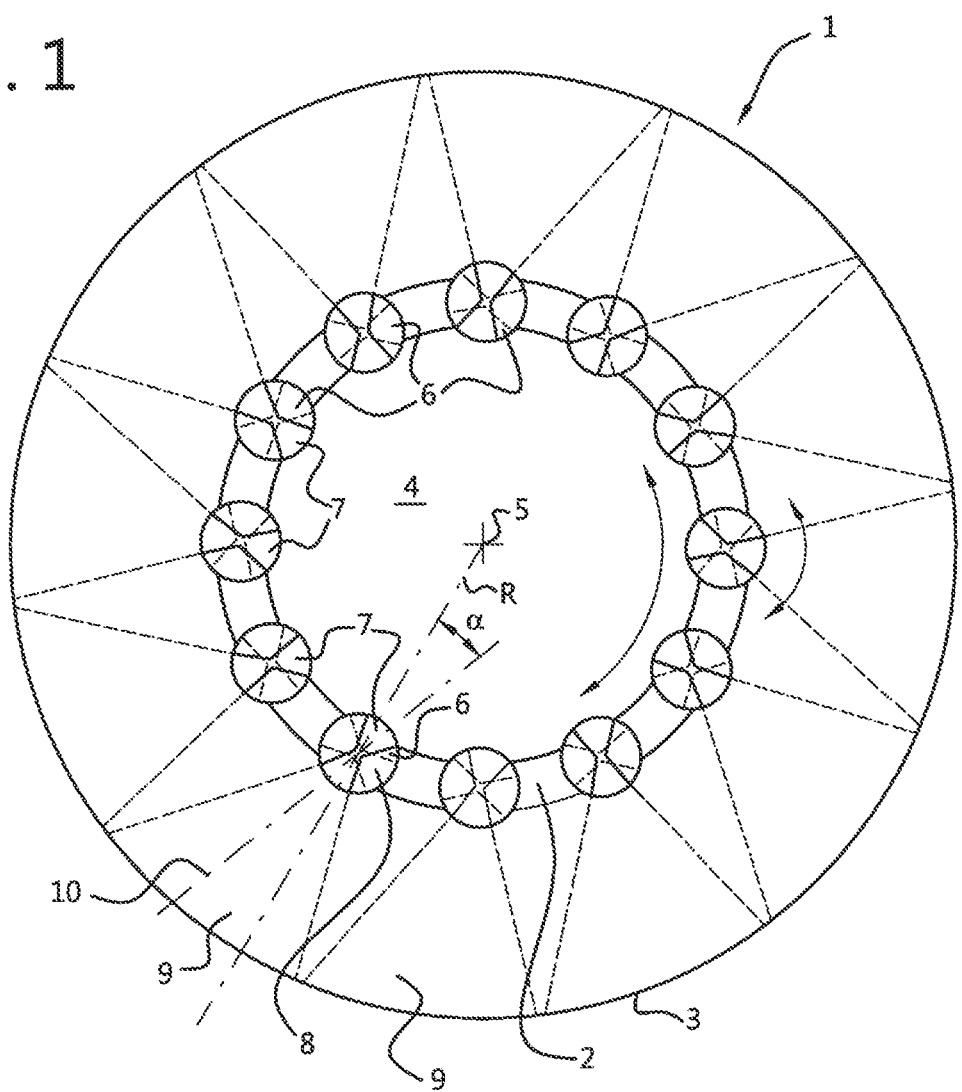
FIG. 1 is a schematic sectional view through a collimator and a detection device of a SPECT scanner according to the invention.

FIG. 1 shows a schematic cross-section through a closed loop-shaped collimator 2 and, at a distance around the collimator, the one or more detectors 3 of the detection device of a SPECT scanner according to the invention (further not shown). This combination is indicated by reference numeral 1, and comprises the collimator 2 and a detector 3 shown here by way of example as a circle.

The collimator 2 surrounds an object space 4 that has a longitudinal direction over the centre line 5 perpendicular to the plane of the figure. In this example, the loop-shaped collimator 2 comprises multiple, here even twelve, rotatable pinhole bodies 6 according to the invention, which are arranged in a circumferential direction of the collimator 2 distributed around the object space 4. The pinhole bodies 6 are each rotatable around a corresponding axis of rotation, which axes of rotation here run parallel and at a distance to the centre line 5. The axes of rotation are thus located around the object space at a distance from one another.

Each pinhole body 6 has, for example, a first pinhole 7 and a second pinhole 8 therein.

One or more further collimator elements of suitable collimator material form the rest of the perimeter of the collimator 2 around the object space.

Figure 2:
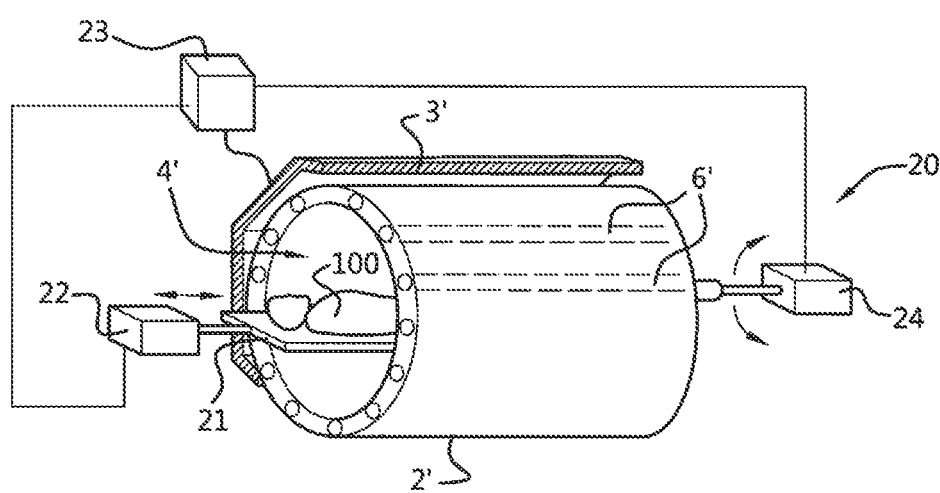
FIG. 2 is a schematic perspective view in partial cross-section of a SPECT scanner according to the invention.

In a possible embodiment, the collimator 2 is configured with a rigid collimator body with a fixed, non-adjustable geometry of the cross-section, for example tubular such as shown in FIGS. 1 and 2, wherein for each rotatable pinhole body, a slot is provided in this fixed collimator body wherein the rotatable pinhole body is arranged. Other embodiments, which for example provide a collimator with an adjustable cross-section, are for example shown in FIGS. 6-11.

Each of the first pinholes 7 projects an image of the object space 4 on the detector 3 at an image angle 9, with a main pass-through direction 10 that here forms an angle α with the radial direction R through the pinhole.

The collimator 2 shown by way of example already offers a number of advantages. For example, each of the pinhole bodies 6 can be rotated such that the respective main pass-through directions 10 of the first pinholes 7 coincide with the respective radial directions 5. In this manner, a collimator 2 is obtained that images a limited, central (focus) volume on the detector 3 with maximum angle data and intensity. By rotating the pinhole bodies 6 to the position shown, the volume imaged on the detector 3 through at least two pinholes indeed becomes greater, so that a greater part of the object can be examined at one time with lower accuracy, but a smaller part thereof (optionally up to no part thereof) can still be imaged by all of the pinholes 7. It is to be noted that the second pinholes 8 here already begin to image a part of the object space on the detector. In order to prevent this, shutter mechanisms can be provided, such as sliders, or shields such as so-called baffles, which block radiation that is at too steep an angle with respect to the detector 3. Incidentally, neither of these mechanisms is shown here in the interest of clarity.

Incidentally, imaging can also be continued during rotation of the pinhole bodies 6. In this way, the respective image angles of the respective pinholes can "brush" or "sweep" through the object space 4. It is advantageous if this takes place in a stepwise manner, wherein an image reconstruction system matrix has been prepared in advance for each position, by means of which the images taken can be converted into 3D data concerning the object located in the object space 4 (not shown here).

Even further rotation of the pinhole bodies 6 to an angle α of 90° causes the second pinholes 8 with their respective main pass-through directions to now be oriented along the radial direction R. These second pinholes 8 have e.g. a higher sensitivity due to a greater average surface area of the pinhole itself. It is also possible for the second pinholes to have a smaller acceptance angle (acceptance angle or opening angle) than the first pinholes. This latter case allows the second pinholes 8 to more sharply image gamma radiation having a higher energy in that the "knife edges" of the pinholes are penetrated to a lesser degree. It is true that only a smaller part of the detector 3 can be covered. It can be particularly useful in the case of such second pinholes 8 to make the collimator 1 rotatable as a whole, such as along the arrow direction shown, for example over an angle of 30°, the angle between two adjacent pinholes.

FIG. 2 is a schematic partial sectional perspective view of an exemplary embodiment of a SPECT scanner 20 according to the invention. In this example, the SPECT scanner 20 comprises an object carrier 21 configured as a lying bed for carrying an object 100, such as a human or in a possible variant a small animal for a preclinical research, as well as a displacement unit 22 under the control of a control unit 23.

The carrier 21 can be brought with the object 100 into the object space 4', which is surrounded by the collimator 2', which in turn is surrounded by a detector 3', shown here only partially and in cross-section.

In the collimator 2', multiple pinhole bodies 6' are distributed around the perimeter, each of which in this case is rotatable around its own axis in the collimator 2' using respective motorised actuators 24, indicated here only once.

When the carrier 21 with the object 100 is at least partially located in the object space 4', the detector 3', which in practice often completely surrounds the collimator 2', will be able to detect gamma radiation emitted by the object via the pinholes in the collimator 2'. These pinholes are arranged in the rotatable pinhole bodies 6'.

For example, the pinhole bodies 6' can be configured as shown in FIG. 1 or FIGS. 3 and 4, 12-16, which will be explained below.

The images of the detector 3' are processed according to a method known per se by the control unit 23.

After taking the images, and thus obtaining a set of image data, the carrier 21 can be displaced, and/or one or more pinhole bodies 6' can be rotated around their axis of rotation, for example by means of the motor 24, and/or the collimator 2' as a whole can be rotated around a longitudinal axis thereof. The rotation is hereby advantageously carried out in a stepwise manner. In this case, the motor 24 is also optionally a stepper motor. This facilitates the processing of the detector data obtained into 3D images of the object 100.

Figure 3:
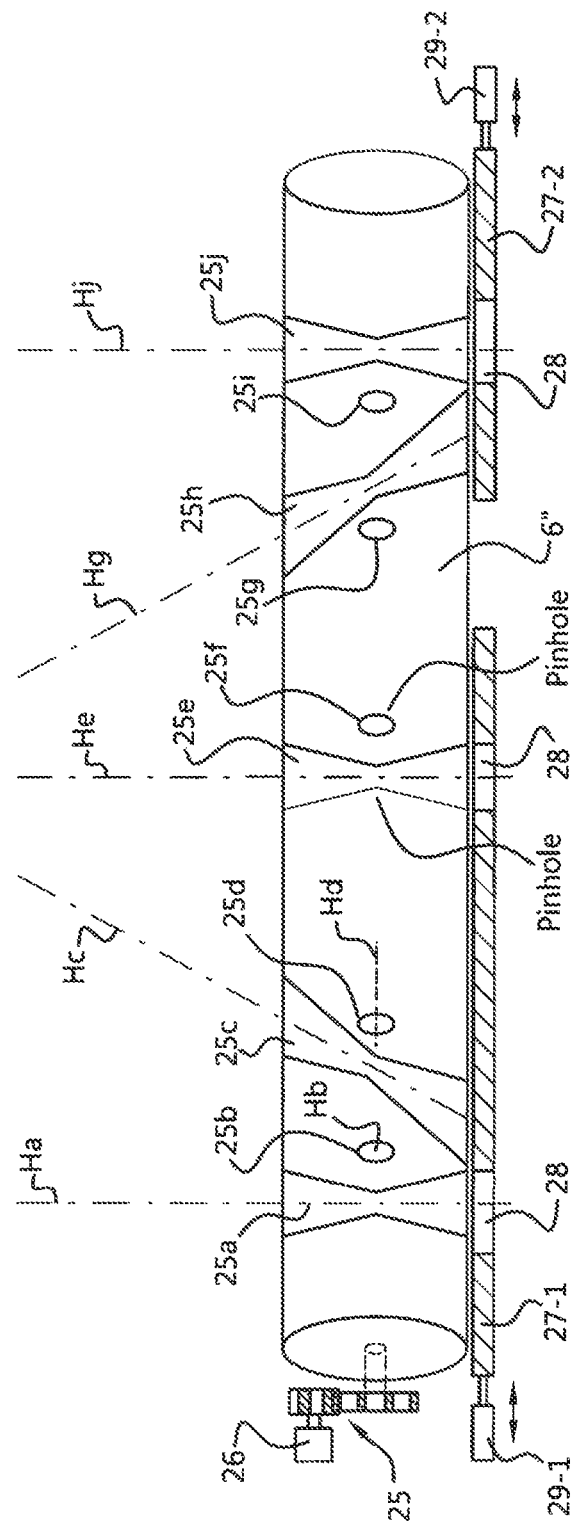
FIG. 3 is a schematic view of a pinhole body of a SPECT scanner according to the invention.

FIG. 3 is a schematic view of a pinhole body 6" that comprises ten pinholes 25a-j with respective main pass-through directions Ha-j and can rotate with a transmission 25 and a motor 26 in a collimator not shown here in further detail.

Moreover, plates 27-1 and 27-2 with openings 28 (between the shaded parts) are shown here by way of example that can be displaced in the directions indicated by the arrows using respective actuators 29-1 and 29-2.

The main pass-through directions Ha, He and Hj of the respective pinholes 25*a*, 25*e* and 25*j* are parallel in this case so that these pinholes together can cover a large volume. The same applies for the pinholes 25*b*, *f* and *i*, which also comprise parallel main pass-through directions, albeit rotated over 90°.

In contrast, the main pass-through directions of the pinholes 25*c*, 25*e* and 25*g* are focused on one point, so that these three pinholes all view a compact focus volume from quite a large number of angles. By rotating the pinhole body 6" by means of the transmission 25 and the actuator 26, it is possible for this focus volume to brush/sweep through an object space. The main pass-through direction Hd of pinhole 25*d* and the corresponding main pass-through directions of pinholes 25 *f* and *g* are also focused on one point. The pinholes 25*a, e* and *j*, as well as c and g, hereby have e.g. a first sensitivity/average surface area or acceptance angle, while the pinholes 25*b, d, f, g*, and *i* e.g. have e.g. another, lower or higher sensitivity/average surface area or acceptance angle. In this manner, the desired properties of the active, open pinholes can be selected by rotating the pinhole body 6".

The main pass-through directions of the pinholes 25*a, c, e, g* and *j* lie in one plane, the plane of the drawing. The main pass-through directions of the other five pinholes 25*b, d, f, g* and *i* lie in the plane perpendicular thereto, i.e. along the axis of rotation of the pinhole body and perpendicular to the plane of the drawing. The projections of the main pass-through directions of these five pinholes on a plane perpendicular to the axis of rotation thus form an angle of 90° with the projections of the main pass-through directions of the former five pinholes 25*a, c, e, g, j* on said perpendicular plane. When the pinhole body 6" is rotated over 90°, the latter are to move to a closed position, and the other five pinholes from a closed position to an open position. In order to prevent the parallel and the focused pinholes from interfering with one another the slides 27-1 and 27-2 are provided, which comprise (frame) holes 28. By suitably moving the slides 27 by means of the actuators 29-1 and 29-2, the pinholes that must allow the radiation to pass through can be selected. For this purpose, of course, the material of the slides 27 is selected to be radiation-absorbing, as is that of the pinhole body 6" itself, for example (hardened) lead. Incidentally, it is easily possible in practice to drill the pinholes 25 and the holes 28 in said hardened lead material.

Figure 4:
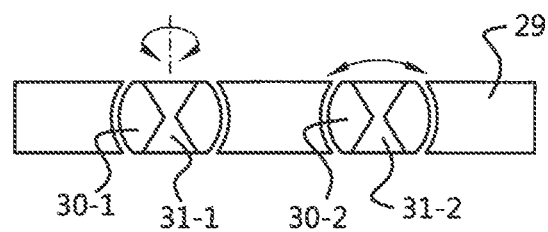
FIG. 4 is a schematic detail view of a small part of a collimator according to the invention.

FIG. 4 shows a schematic detail of a small part of a collimator, with two pinholes 30-1 and 30-2 therein, each of which is arranged in its own pinhole body 31-1 and 31-2 respectively.

Both pinhole bodies 31-1 and 31-2 are spherical, cut on two sides where material is removed for the pinholes, and can in principle rotate in all directions in the collimator part 29, wherein two relevant directions are indicated by the arrows. Such an arrangement provides the collimator with maximum flexibility but also complexity. It is to be clear that a cylindrical pinhole body provides fewer degrees of freedom, but is significantly simpler to operate and requires less complex calculations in the image processing.

Figure 5:
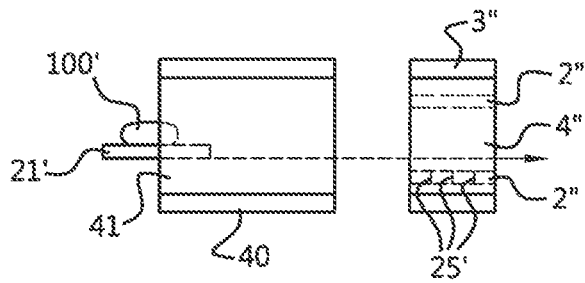
FIG. 5 is a schematic view of a combination of a first scanner and a system according to the invention.

FIG. 5 shows a schematic view of a combination of a first scanner 40 and a system according to the invention, comprising a collimator 2" and a detection device 3" for detecting gamma radiation that is allowed to pass out of the object space 4" through one or more of the pinholes 25.'

The first scanner 40 has an object space 41 as well as an object carrier, for example a bed 21' that carries an object 100' thereon. The carrier is moveable through the object space in the direction of the dashed arrow. This first scanner 40 can in principle be any type of scanner, such as an (x-ray) CT scanner or an MRI scanner.

A system according to the invention is placed behind the first scanner, with a detection device 3" and therein a collimator 2" provided with pinholes 25' around an object space 4". Here, the object space 4" is continuous with the object space 41, so that the bed 21' with the object 100' can be successively examined by the first scanner 40 and the gamma scanner 2", 3" according to the invention. An advantage of this arrangement is that the gamma scanner 2", 3" can thus easily be coupled to an existing scanner 40. The only change that has to be made is lengthening of the path of the bed 21'. Of course, the collected image data must be processed.

For this purpose, a separate processing device may be provided, but the data may optionally be processed by the suitably adapted processing device of the first scanner 40.

Figure 6A:
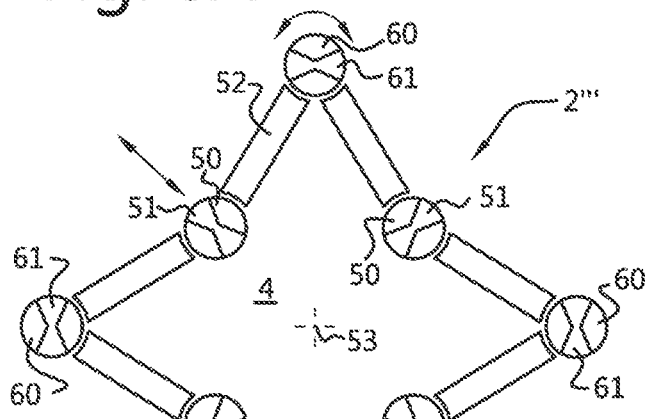
FIGS. 6*a, b* are schematic side views of a first (FIG. 6*a*) and a second (FIG. 6*b*) position of a collimator according to the invention.

FIG. 6*a, b* shows a schematic side view of a first (FIG. 6*a*) and a second (FIG. 6*b*) position of a collimator 2''' of a SPECT scanner according to the invention.

FIG. 6*a* shows the collimator 2''' in a first position. The collimator comprises here by way of example four first rotatable pinhole bodies 50, each with one or more first pinholes 51, and here by way of example, four second pinhole bodies 60, each with one or more second pinholes 61. 52 indicates by way of example eight mutually pivotable collimator elements, and 53 indicates the centre of the object space 4.

In the first position shown in FIG. 6*a*, the collimator 2''' has a four-pointed star shape, wherein in this example, moreover, the four first rotatable pinhole bodies 50 with their first pinholes 51 are rotated to an open position and lie closer to the centre 4 than the second pinhole bodies 60 with the second pinholes 61, which are shown here in a closed position. In this case, therefore, only the first pinholes 51 project an image on the detector (not shown).

Figure 6B:
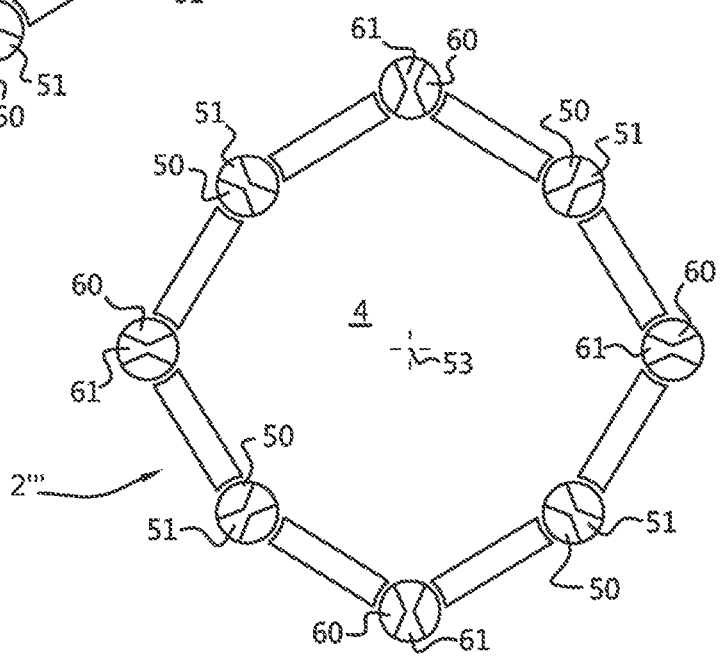

The collimator 2''' can be brought in the second position of FIG. 6*b* by mutually pivoting the collimator elements 52 along the direction of the double arrows in FIG. 6*a* so that they move relatively to the outside. For this purpose, collimator element displacement units are provided that are not shown here, but which, for example, comprise actuators that are mounted on the axial ends of the collimator elements, seen in longitudinal direction of the collimator/object space.

In FIG. 6*b*, the collimator 2''' now roughly forms a circle (more accurately: an octagon, but note that the elements could also be a circle arc of 0.25π in order to form a circle). The pinhole bodies 50 and 60 lie on or in the immediate vicinity of the pivot lines between adjacent elements 52. The first pinholes 51 of the first pinhole bodies 50 thus lie farther away from the centre 53, and in this example as far as the second pinholes 61. In order to prevent a large part of the detector from remaining unused, with the result that too little data would be collected, the second pinhole bodies 60 are now preferably rotated with the second pinholes 61 into an active position, for example over a quarter turn. There are now twice as many pinholes available, so that good images can still be made even at the increased distance from the centre 53. In this manner, the collimator and/or SPECT scanner is suitable for objects of different size in the object space 4, without requiring that the relevant carrier be displaced or even that the collimator be exchanged.

Figure 7:
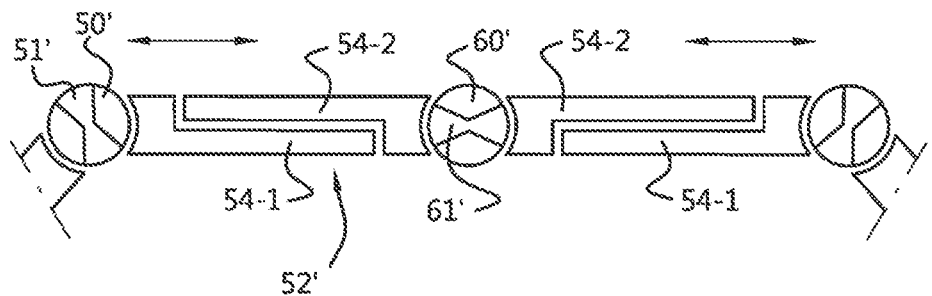
FIG. 7 is a view of a part of an alternative collimator according to the invention.

FIG. 7 shows a part of an alternative collimator with variable cross-sectional dimensions. In this case, instead of pivoting collimator elements 52, the collimator 2''' is provided with elements 52 each of which comprises two part elements 54-1 and 54-2 that are mutually slideable in the direction of the double arrows. In this manner, the length of a collimator element 52 increases, and thus the cross-section of the collimator. Again, this can be compensated for by rotating pinholes, in this case the second pinholes 61' of second pinhole bodies 60'. Both the rotation of pinhole bodies 60' and the sliding of the part elements 54-1 and 54-2 are carried out using actuators suitable for this purpose that are not shown, such as electrical, either linear or non-linear actuators.

Figure 8:
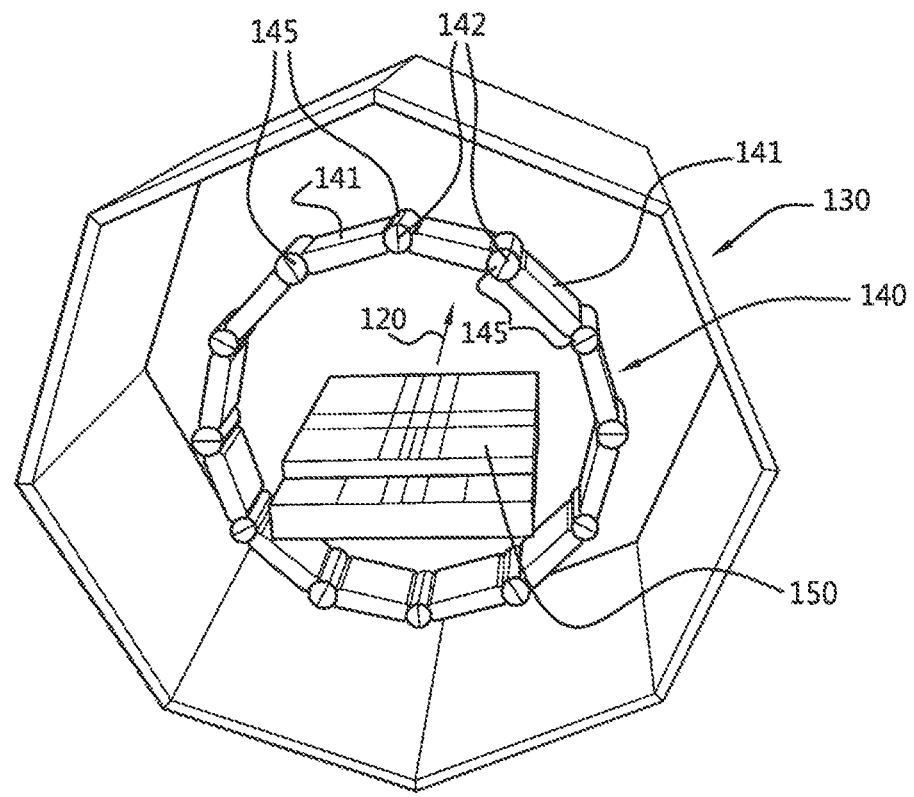
FIG. 8 is a schematic view of the detectors, collimator, and object carrier of an embodiment of a SPECT scanner according to the invention.

FIG. 8 is a schematic view of the detectors 130, collimator 140, and object carrier 150 of an embodiment of a SPECT scanner according to the invention. The collimator 140 comprises multiple collimator elements 141 arranged in a series that extends, in a circumferential direction seen from the collimator, at least partially around the longitudinal direction 120 of the imaging space. The adjacent collimator elements 141 of the series are in this case pivotable with respect to one another, in this example mutually connected by a pivot mechanism 148 forming a pivot axis 142 that runs parallel to said longitudinal direction. One rotatable pinhole body 145 each is arranged between adjacent collimator elements of the series, which pinhole body 145 is rotatable with respect to the adjacent collimator elements 141 around an axis of rotation that extends essentially parallel to said longitudinal direction and here coincides with the axis 142.

The cross-section of the collimator 140 perpendicular to the longitudinal direction 120 is adjustable by pivoting the collimator elements 141, for example from a more or less circular shape to an oval shape, for example a horizontal oval shape, for example such that the collimator 140 can be partially brought close to the anterior side and the posterior side of the torso of a patient lying on the carrier 150. This shape adjustment of the collimator 140 is preferably not followed by the one or more detectors 130, which in the context of the present invention preferably have a fixed cross-section, such as a triangular arrangement (for example for imaging of small animals) or a polygonal or more or less circular arrangement.

Figure 9:
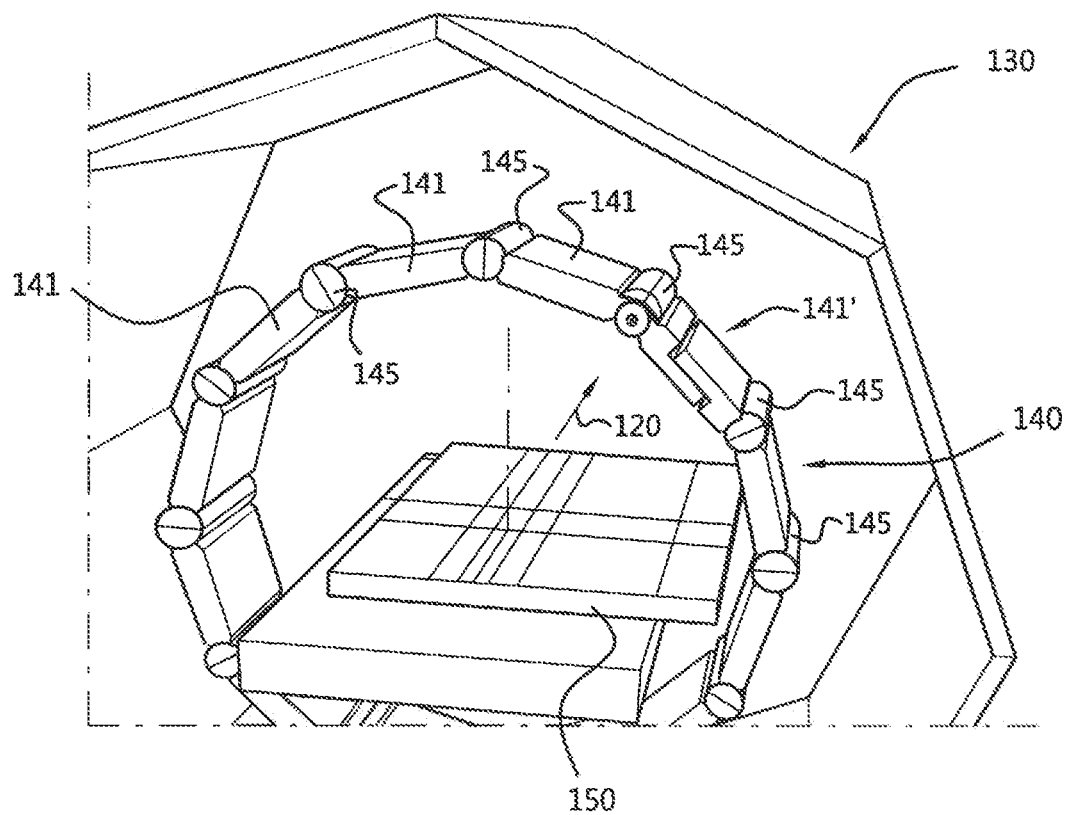
FIG. 9 is a schematic view of the detectors, collimator, and object carrier of another embodiment of a SPECT scanner according to the invention.
Figure 10:
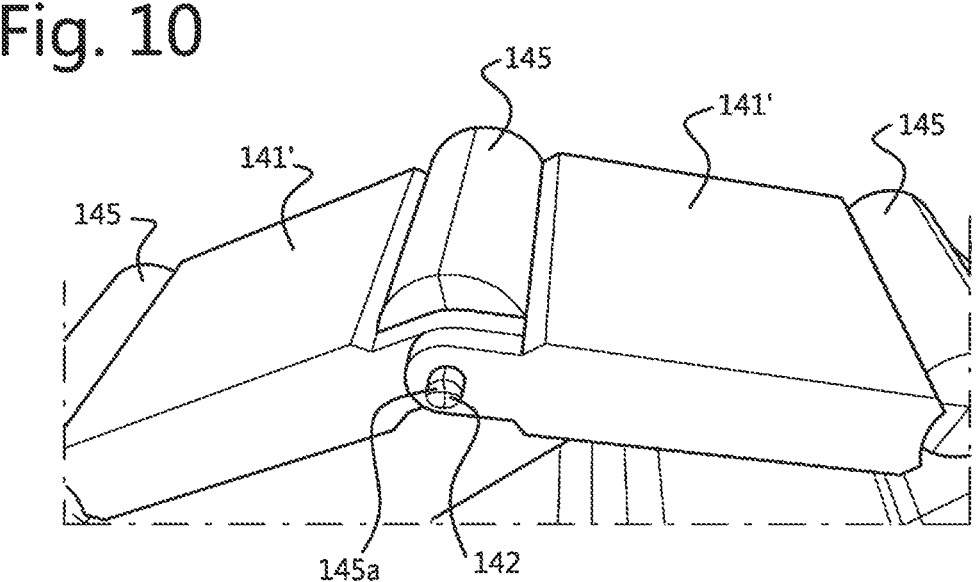
FIG. 10 is a larger-scale schematic view of the collimator of the SPECT scanner of FIG. 9.
Figure 11:
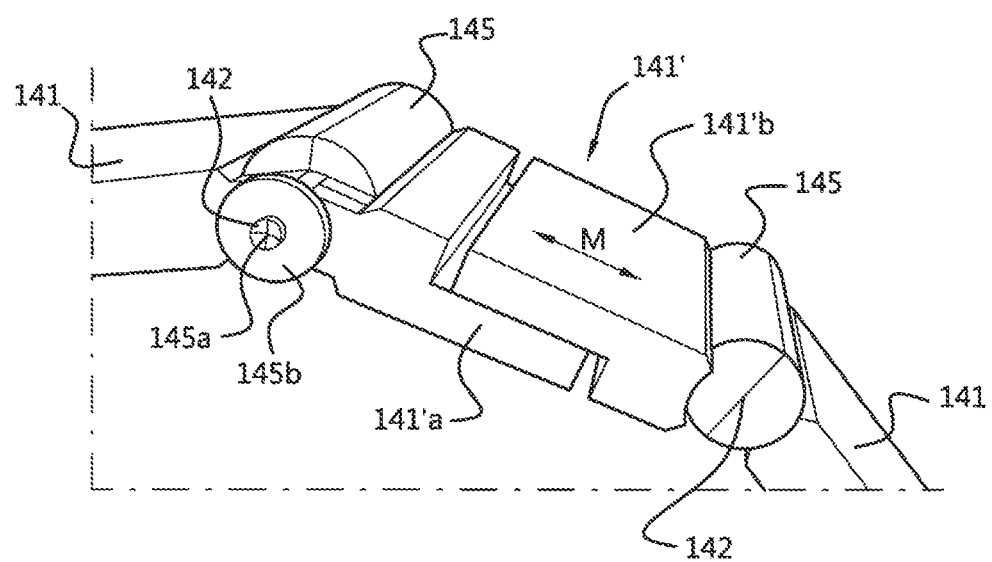
FIG. 11 is a larger-scale schematic view of the collimator of the SPECT scanner of FIG. 9.

FIGS. 9, 10, and 11 illustrate possible details of the SPECT scanner and collimator according to the invention.

In a simple version, the carrier 150 is adjustable only in the longitudinal direction, and optionally in the height direction. In a further variant, the carrier 150 is also moveable sideways, i.e. in FIG. 8 to the left or right. This is shown in FIG. 9 and can for example be used in order to position a region of interest more toward or completely in the centre of the imaging space, for example the heart of a patient.

FIG. 10 shows that the adjacent collimator elements 141' are connected to one another by a pivot mechanism 148. In this case as well, it can be seen that the rotatable pinhole body 145 is provided on one axial end thereof with an engagement element for the rotation drive, here a stub axle 145a, on which a wheel, such as a toothed wheel 145b, can be mounted.

FIG. 11 shows that the collimator element 141', seen in the circumferential direction, is adjustable in width. It is shown here that the collimator element 141' comprises a first sub-element 141'a and a second sub-element 141'b that at least partially overlap each another and that are slideable with respect to each other, cf. arrow M, such that the width of the collimator element 141' is adjustable. For example, one or more actuators is/are provided that are configured for adjusting the width of collimator element 141'. The thickness of the first sub-element 141'a and the second sub-element 141'b can, optionally locally, be adapted to this adjustability in order to ensure that the radiation is blocked.

FIGS. 12a, b show schematic sectional views of an alternative collimator according to the invention, shown with the elongated pinhole body rotatable around one axis in a first position, FIG. 12a, and a second position, FIG. 12b.

Reference numeral 4 indicates the object space of a SPECT scanner, further not shown, for making images of an object using gamma radiation. As shown in FIG. 1, for example, the scanner comprises:
- an object space 4 with a longitudinal direction (here transverse to the plane of the image),
- an object carrier configured for bringing an object into the object space in said longitudinal direction and for positioning the object in the object space,
- the collimator that at least partially extends around the object space, wherein the collimator comprises a set of multiple pinholes, each of which comprises a field of view with a main pass-through direction for the gamma radiation,
- a detection device with at least one detector configured for detecting gamma radiation that is allowed to pass through from the object space by one or more of the pinholes, wherein the collimator is provided between the object space and the at least one detector.

It is shown in further detail that the collimator is provided with at least one rotatable pinhole body 6' with at least one pinhole therein 7', for example one or more rows of pinholes in the longitudinal direction of the body 6'.

The elongated pinhole body 6' is rotatably arranged around a corresponding axis of rotation 6'a extending in a longitudinal direction between adjacent collimator elements 2a,b.

For example, as shown, the collimator elements 2a, b are provided with circular arc-shaped size edges between which the pinhole body 6' is rotatably arranged. Preferably, the planes of the body 6' adjacent to the side planes in the first and second position of the body 6' have a corresponding circular arc-shaped configuration. An embodiment of the side edges of the elements 2a, b having a C-shaped cross-section and/or another cross-sectional shape of the adjacent planes of the body 6' is e.g. also conceivable.

For example, the adjacent collimator elements 2a, 2b form part of a loop-shaped collimator 2, for example with a polygonal cross-sectional shape, that can or cannot be varied in shape.

For controlling the rotation of the pinhole body 6' around its axis 6'a, possibly by means of a control unit, a pinhole body rotation device 24, which is shown in FIG. 2, can be provided.

It can be seen that that the pinhole 7 extends from a first opening 7a on a first side of the pinhole body to a second opening 7b on a second side of the pinhole body located opposite the first side.

It can be seen that that the pinhole 7 has a smallest cross-sectional part 7c that defines the smallest cross-section for gamma radiation of the pinhole 7 and that is located at a distance from the first opening 7a and the second opening 7b of the pinhole. This part 7c can form a knife edge, but part 7c can e.g. also form a short channel with a small cross-section.

It can be seen that that the pinhole 7 comprises a double cone with part 7c in between. The one cone extends from part 7c to the first opening 7a, and the other, second cone extends from part 7c to the second opening 7b. The shape of the cones can be suitably selected, for example with a circular cross-section or with a rectangular cross-section, which shape is also known as a loft pinhole.

It can be seen that that the smallest cross-sectional part, seen in the direction between the first opening 7a and the second opening 7b of the pinhole, is located at a distance away from the axis of rotation 6'a of the pinhole body.

It can be seen that that each of the collimator elements 2a, b that are adjacent to the rotatable pinhole body 6 has an object space side and a detector side that respectively are adjacent to the object space and face toward the detector. Between the object space side and the detector side, a thickness of the collimator elements 2a, b is defined. The dashed line shows an imaginary centre plane through the centre of the thickness.

It can be seen that the axis of rotation 6'a of the pinhole body in this example lies on the centre planes of the adjacent collimator elements, which in this example lie in each other's direction of extension. Other positions with respect to the centre planes are also conceivable.

It can be seen that that the pinhole body 6'a has an essentially circular segment-shaped cross-section with an essentially flat first side 7d and a circular arc-shaped second side 7e. The arc of the circle preferably extends over more than 180°.

It can be seen that that the first side 7d of the pinhole body is at a smaller distance from the axis of rotation 6'a than the second side 7e.

It can be seen that that the smallest cross-sectional part 7c of the pinhole 7 lies farther away from the first side 7d than the distance to the second side 7e.

It can be seen that that the diameter of the circular segment-shaped pinhole body 6 is greater than the thickness of the adjacent collimator parts 2a, b.

The view in FIG. 12a shows the pinhole body 7 when it is rotated with the second side toward the object space 4. FIG. 12b shows the pinhole body 7 when it is rotated with the first side toward the object space 4.

It can be clearly seen from FIGS. 12a and 12b that during use of the collimator, the distance between the smallest cross-sectional part 7c of the pinhole 7 and an object positioned by the object carrier is variable by selectively rotating the pinhole body 6' with the first side 7d thereof or with the second side thereof 7e toward the object space 4.

The extent of variation that can be obtained in this simple manner depends on the selected dimensions of the relevant components and the position of the axis of rotation 6'a.

It can be seen more clearly from FIGS. 12a and 12b that during use of the collimator, the space available for an object within the collimator 2 can be varied by selective rotation of the pinhole body 6 with flat side 7d. For example, a relatively large object, for example a part of a person, can be arranged in the collimator in the position of FIG. 12b because the flat side 7d then lies close to, or optionally in a common plane with, the object side of the adjacent collimator parts 2a,b. For imaging of a smaller object, the configuration of FIG. 12a can then be used, wherein the collimator makes it possible, for example for both a relatively large object and a relatively small object, to position the part 7c as close as possible to the object.

FIG. 13a shows a sectional and perspective view of a collimator part, for example of a loop-shaped collimator 2, with the rotatable pinhole body 6' therein in the first position of FIG. 12a. The dashed-line circle for reference in that body 6' clearly shows that the part 7c is located farther from the flat side 7d than the distance to the opposite side 7e, which is circular arc-shaped is in this example. For illustrative purposes, FIG. 13a shows on the right side a pinhole body 6 with a cylindrical perimeter and with the part 7c in the centre of that body 6 coinciding with the axis of rotation thereof. In the embodiment, rotation of the body 6 can adjust the direction in which radiation passes through, but there are no further effects compared to the effects of the pinhole body 6'.

FIG. 13b shows the other rotation position of the rotatable pinhole body 6' with the second side 7e toward the object space 4.

It will be apparent that the first and/or the second position of the rotatable pinhole body 6' does not have to exclusively refer to one specific angle of the body 6'. If desired, each of these positions can also comprise an angle range so that the main direction of the pinhole 7 is optimally adjustable within that range.

Figure 14:
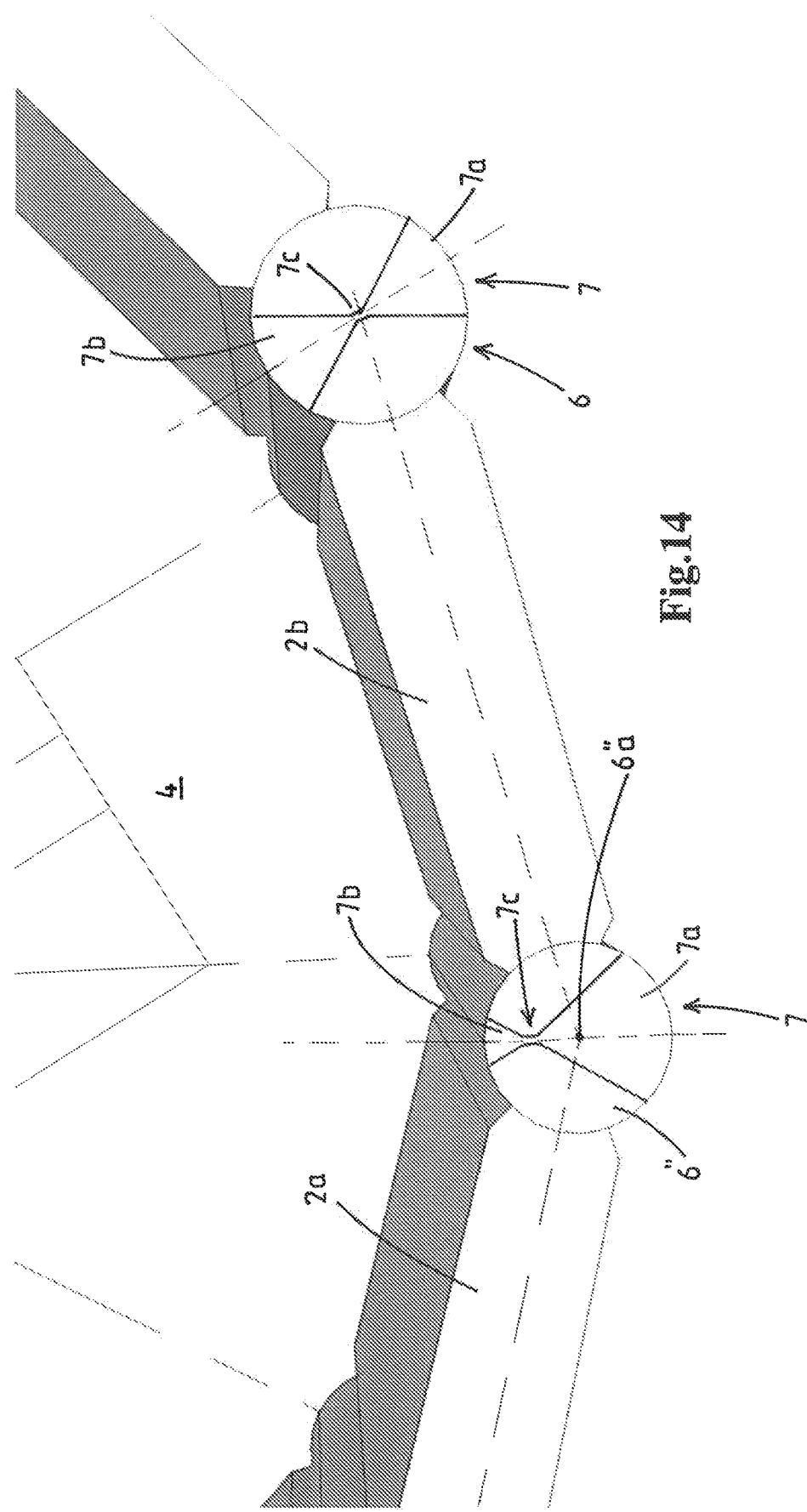
FIG. 14 is a sectional view of an alternative collimator according to the invention with two different rotatable pinhole bodies.

FIG. 14 shows a sectional and perspective view of an alternative collimator according to the invention with two different rotatable pinhole bodies 6, 6". Here, the two pinhole bodies have a cylindrical cross-section.

In pinhole body 6" a pinhole 7 is located, part 7c of which lies out of centre with respect to the two openings 7a, 7b of the pinhole. Said part 7c is therefore eccentric with respect to the axis of rotation 6"a.

In pinhole body 6 a pinhole 7 is located, part 7c of which lies in the centre with respect to the two openings 7a, 7b of the pinhole. Furthermore, said part 7c lies on the axis of rotation.

The comparison of the two pinhole bodies 6, 6" shows that in body 6", the rotation to the second position described herein also results in a variation of the distance of part 7c from the object carrier and object positioned thereby (if present). This is not the case for body 6, wherein rotation can only produce a change in the main direction of the pinhole 7.

As mentioned above, pinhole bodies 6', 6" can be applied in a loop-shaped collimator, for example a collimator variable in shape such as described herein.

Figure 15:
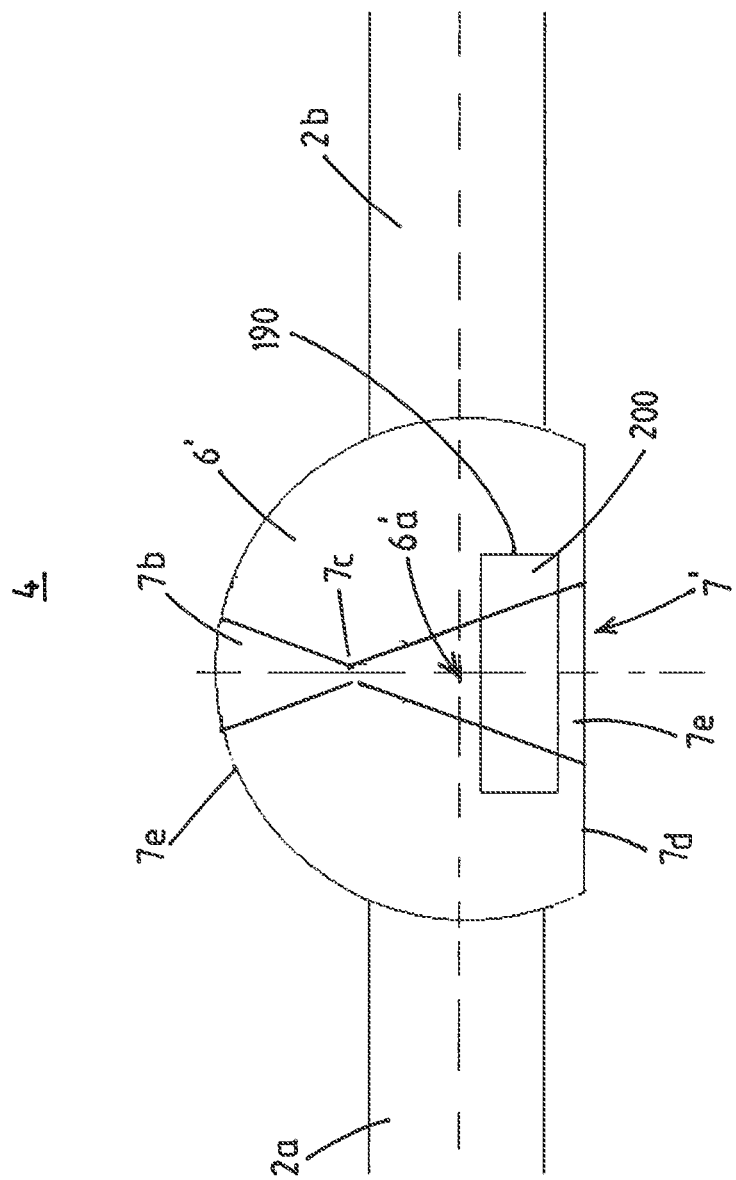
FIG. 15 is a sectional view of the collimator of FIGS. 12a,b, provided with a shutter element for the selective blocking of the field of view of a pinhole.

FIG. 15 is a schematic view of a cross-section of the collimator of FIG. 12a,b, provided with a shutter element 200 for the selective blocking of the field of view of a pinhole 7'.

Shown is a pinhole body 6' that is elongated and rotatable around one axis of rotation provided with a recess 190 extending over at least one part of the length thereof, wherein the field of view of at least one pinhole 7', preferably of a group pinholes, extends through the recess 190.

It can be seen that that the recess 190 is configured as an elongated internal channel in the inside of the body 6' and extending in a longitudinal direction therein.

It is schematically shown that a shutter element 200 that fits into the recess is provided as an elongated rod that is configured to block, in a working position thereof, the field of view of the at least one pinhole 7'.

For example, the shutter element 200 has one or more holes distributed over its length that correspond to the location of the one or more pinholes 7' in the body 6'.

For example, the shutter element 200 is linearly displaceable, optionally by means of a corresponding actuator, between an opened position of the pinhole(s) wherein the one or more holes are aligned with the one or more pinholes, for example the holes form a part of the pinhole other than the part with the smallest passage, and a closed position wherein a radiation-impermeable part of the shutter element blocks the pinhole from allowing radiation to pass through. Optionally, the one or more holes in the shutter element are filled with a radiation-permeable material.

In another variant, the shutter element is removable as a whole from the body 6', for example at an axial end of the pinhole body 6', in order to provide the opened position, e.g., a radiation-permeable element is then present in the recess 190, composed for example of plastic.

The invention claimed is:

1. A SPECT scanner for making images of an object using gamma radiation emitted by the object, comprising:
   an object space with a longitudinal direction;
   an object carrier configured for bringing an object into the object space in said longitudinal direction and for positioning the object in the object space;
   a collimator that extends in a circumferential direction thereof at least partially around the object space, wherein the collimator comprises a set of multiple pinholes each of the set of multiple pinholes comprising a field of view with a main pass-through direction for gamma radiation emitted by the object; and
   a detection device with at least one detector configured for detecting gamma radiation that is allowed to pass through from the object space by one or more of the pinholes, wherein the collimator is provided between the object space and the at least one detector,
   wherein the collimator is provided with at least one rotatable pinhole body with at least one pinhole therein, the pinhole body being rotatably arranged in the collimator around at least one corresponding axis of rotation.

2. The SPECT scanner according to claim 1, wherein the collimator comprises multiple rotatable pinhole bodies that are arranged around the object space distributed in the circumferential direction, each of the rotatable pinhole bodies having at least one pinhole therein,
   wherein each rotatable pinhole body is rotatably arranged in the collimator for rotation around at least one corresponding axis of rotation,
   wherein the axes of rotation of the pinhole bodies are apart from one another, and
   wherein each rotatable pinhole body is rotatably arranged in the collimator exclusively around an axis of rotation that extends essentially parallel to said longitudinal direction.

3. The SPECT scanner according to claim 1, wherein the collimator in the circumferential direction thereof forms a closed loop around the object space,
   wherein multiple rotatable pinhole bodies are provided in the collimator distributed in the circumferential direction, each of the rotatable pinhole bodies having at least one pinhole therein,
   wherein each rotatable pinhole body is rotatably arranged in the collimator for rotation around at least one corresponding axis of rotation, and
   wherein each rotatable pinhole body is rotatably arranged in the collimator exclusively around an axis of rotation that extends essentially parallel to said longitudinal direction.

4. The SPECT scanner according to claim 1, wherein the collimator, seen in the circumferential direction thereof, comprises a series of multiple collimator elements and at least one rotatable pinhole body, and
   wherein said rotatable pinhole body is arranged between adjacent collimator elements, the rotatable pinhole body having at least one pinhole therein and being rotatably arranged in the collimator for rotation around one corresponding axis of rotation that extends essentially parallel to said longitudinal direction.

5. The SPECT scanner according to claim 4, wherein adjacent collimator elements of the series of multiple collimator elements are pivotable with respect to one another around a pivot axis that extends essentially parallel to said longitudinal direction,
   wherein adjacent collimator elements are interconnected by a pivot mechanism that forms a pivot axis running parallel to said longitudinal direction, and
   wherein a cross-section of the collimator perpendicular to the longitudinal direction is adjustable by pivoting the collimator elements.

6. The SPECT scanner according to claim 1, wherein the rotatable pinhole body is configured as an elongated solid rod of collimator material, the rod being rotatable in the collimator for rotation around a longitudinal axis thereof.

7. The SPECT scanner according to claim 1, wherein the collimator is provided with at least one rotatable pinhole body with at least one pinhole therein, wherein the at least one pinhole extends from a first opening on a first side of the pinhole body to a second opening on a second side of the pinhole body located opposite the first side,
   wherein the at least one pinhole has a smallest cross-sectional part that defines the smallest cross-section for gamma radiation of the pinhole and is located at a distance from the first opening and the second opening of the pinhole, and
   wherein the smallest cross-sectional part, seen in a direction between the first opening and the second opening of the pinhole, is located at a distance from the axis of rotation of the pinhole body, such that during use a distance between the smallest cross-sectional part of the pinhole and an object positioned by the object carrier is variable by selectively rotating the pinhole body with the first side thereof or the second side thereof toward the object space.

8. The SPECT scanner according to claim 1, wherein the at least one axis of rotation of the pinhole body in the collimator extends essentially parallel to said longitudinal direction, and
   wherein the pinhole body is rotatably arranged in the collimator exclusively around an axis of rotation that extends essentially parallel to said longitudinal direction.

9. The SPECT scanner according to claim 1, wherein said set of multiple pinholes of the collimator comprises two or more sub-sets, each of the sub-sets comprising one or multiple pinholes, and
   wherein the collimator is provided with at least one rotatable pinhole body comprising pinholes that belong to two or more of said sub-sets.

10. The SPECT scanner according to claim 1, wherein the at least one pinhole body comprises one or more first pinholes with one or more first properties and also comprises one or more second pinholes, and
    wherein the one or more first pinholes comprise(s) a first acceptance angle, and the one or more second pinholes comprise(s) a second acceptance angle, wherein the second acceptance angle is smaller than the first acceptance angle.

11. The SPECT scanner according to claim 1, wherein multiple first pinholes are provided in the rotatable pinhole body,
    wherein at least two first pinholes in said pinhole body comprise mutually parallel main pass-through directions,
    wherein multiple second pinholes are provided in said pinhole body, and wherein at least two second pinholes comprise main pass-through directions running toward each other in said longitudinal direction.

12. The SPECT scanner according to claim 1, wherein the at least one pinhole body comprises one or more first pinholes with one or more first properties, and also comprises one or more second pinholes,
wherein the one or more first pinholes comprise(s) a first sensitivity and a first main pass-through direction, and the one or more second pinholes comprise(s) another second sensitivity and a second main pass-through direction, and
wherein respective perpendicular projections of the first main pass-through direction and the second main pass-through direction on a plane perpendicular to the axis of rotation of the pinhole body mutually include an angle of at least 60°.

13. The SPECT scanner according to claim 1, wherein each pinhole body is configured as a solid rod that is rotationally symmetrical around the corresponding axis of rotation.

14. The SPECT scanner according to claim 1, further comprising:
a pinhole body rotation device that is configured for rotating one or more of the pinhole bodies around the respective axis of rotation; and
a control unit for controlling the pinhole body rotation device.

15. The SPECT scanner according to claim 1, wherein the object carrier is configured for carrying a person in a lying position and wherein the scanner is configured for imaging a part of the person.

16. The SPECT scanner according to claim 1, wherein the collimator extends entirely around the object space in the form of a closed loop.

17. The SPECT scanner according to claim 1, wherein the collimator comprises at least four collimator elements arranged in a series that extend around the longitudinal direction of the object space seen in the circumferential direction of the collimator,
wherein adjacent collimator elements of the series are pivotable with respect to one another,
wherein adjacent collimator elements of the series are interconnected by a pivot mechanism that forms a pivot axis running parallel to said longitudinal direction,
wherein one pinhole body is arranged between adjacent collimator elements of the series, the one pinhole body being rotatable with respect to the adjacent collimator elements around an axis of rotation that extends essentially parallel to said longitudinal direction, and
wherein a cross-section of the collimator perpendicular to the longitudinal direction is adjustable by pivoting the collimator elements.

18. The SPECT scanner according to claim 1, wherein a collimator drive is provided that is configured to rotate the collimator over an angle range that is less than a complete rotation around an axis parallel to said longitudinal direction and to position the collimator in discrete angled positions.

19. The SPECT scanner according to claim 1, wherein the SPECT scanner is provided with a detector drive that is configured to rotate the one or more detectors over an angle range that is less than a complete rotation around an axis parallel to said longitudinal direction and to position the one or more detectors in discrete angular positions.

20. The SPECT scanner according to claim 17, wherein multiple pinhole bodies are coupled with a joint drive motor with a transmission to the pinhole bodies for rotating said pinhole bodies, and
wherein multiple collimator elements are coupled with a joint drive motor with a transmission to the collimator elements for pivoting said collimator elements.

* * * * *